United States Patent [19]
Ishizaki et al.

[11] Patent Number: 6,001,911
[45] Date of Patent: Dec. 14, 1999

[54] ABSORBENT RESIN, ABSORBENT MATERIAL AND METHOD OF MANUFACTURING THE SAME

[75] Inventors: Kunihiko Ishizaki, Suita; Hisanobu Obara, Ohda; Toshimasa Kitayama; Yoshihiro Motono, both of Himeji; Nobuyuki Harada, Suita, all of Japan

[73] Assignee: Nippon Shikubai Co., Ltd., Osaka, Japan

[21] Appl. No.: 08/860,445

[22] PCT Filed: Oct. 31, 1996

[86] PCT No.: PCT/JP96/03191

§ 371 Date: Jun. 26, 1997

§ 102(e) Date: Jun. 26, 1997

[87] PCT Pub. No.: WO97/16492

PCT Pub. Date: May 9, 1997

[30] Foreign Application Priority Data

Nov. 2, 1995 [JP] Japan ................................. 7-286266
Oct. 14, 1996 [JP] Japan ................................. 8-270917

[51] Int. Cl.$^6$ .................................................. C08K 5/05
[52] U.S. Cl. ..................... 524/388; 521/141; 521/149; 524/556; 524/557
[58] Field of Search ............................................. 524/388

[56] References Cited

U.S. PATENT DOCUMENTS

| | | | |
|---|---|---|---|
| 4,066,583 | 1/1978 | Spaulding | 260/17.4 |
| 4,691,782 | 9/1987 | Stine | 168/12 |
| 4,826,880 | 5/1989 | Lesniak et al. | 521/53 |
| 4,920,202 | 4/1990 | Irie et al. | 528/500 |
| 5,075,344 | 12/1991 | Johnson | 521/140 |
| 5,135,475 | 8/1992 | Nakanishi | 604/14 |
| 5,145,906 | 9/1992 | Chambers et al. | 524/732 |
| 5,262,894 | 11/1993 | Wheatley | 359/586 |
| 5,278,694 | 1/1994 | Wheatley | 359/359 |
| 5,366,793 | 11/1994 | Fitts | 428/198 |
| 5,385,775 | 1/1995 | Wright | 428/284 |
| 5,428,076 | 6/1995 | Roe | 521/53 |
| 5,518,761 | 5/1996 | Hatsuda et al. | 427/180 |
| 5,700,254 | 12/1997 | McDowall | 604/378 |
| 5,753,452 | 5/1998 | Smith | 435/14 |
| 5,853,867 | 12/1998 | Harada et al. | 428/317.9 |

FOREIGN PATENT DOCUMENTS

| | | |
|---|---|---|
| 6-306202 | 11/1994 | European Pat. Off. . |
| 0 648 800 A2 | 4/1995 | European Pat. Off. . |
| 7-112129 | 5/1995 | Japan . |
| 7-216244 | 8/1995 | Japan . |

*Primary Examiner*—Paul R. Michl
*Attorney, Agent, or Firm*—Kubovcik & Kubovcik

[57] ABSTRACT

A water content of a water-containing gel of a hydrophilic cross-linked polymer is reduced by pressuring (calendaring) it. Then, a gel composition including, for example, a water-containing gel including cross-linked poly(meth)acrylic acid (salt), glycerol (polyhydric alcohol) and polyester fibers (auxiliary forming material), etc., is fed to a drum dryer on an upstream side of a pressurizing roller. Then, the resulting gel composition is pressurized (calendared) heated by a pressurizing roller to be formed into a sheet. As a result, a sheet-like absorbent material having at least one smooth surface can be obtained. The absorbent material resulting from the described method shows excellent properties and especially absorbing properties such as absorbing rate, absorbency under load, and shape retaining properties.

46 Claims, 4 Drawing Sheets

FIG.2(a)
FIG.2(b)
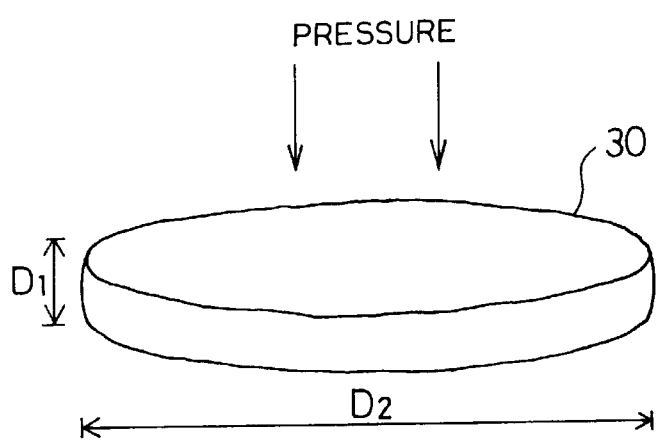
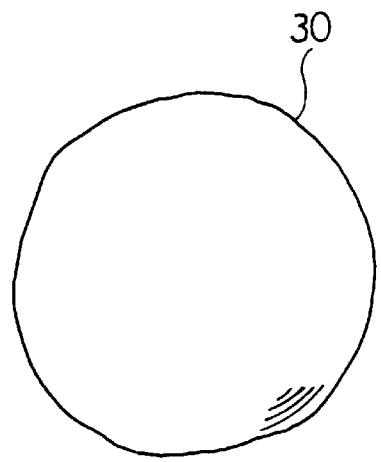

ABSORBENT RESIN, ABSORBENT MATERIAL AND METHOD OF MANUFACTURING THE SAME

FIELD OF THE INVENTION

The present invention relates to absorbent resins and absorbent materials which are suited for use in sanitary materials such as paper diapers (disposable diapers), sanitary napkins, so-called incontinence pads, etc., moisture condensation absorbent sheets, agricultural water retaining materials, waterproofing agents for civil engineering works, medical materials, such as medical sheets, etc., materials for keeping foodstuffs fresh, and materials for preventing foodstuffs from dripping, etc., and a method of manufacturing such absorbent material.

BACKGROUND OF THE INVENTION

Recently, absorbent materials have been used in a variety of fields, for example, as materials for paper diapers, sanitary napkins, so-called incontinence pads, for the purpose of absorbing body fluids. Generally, such absorbent materials are produced in the following manner. After powdery or granular absorbent resin is sandwiched between layers of paper, etc., processing operations such as an embossing operation are applied to the paper, etc., or after incorporating absorbent resin with pulp, etc., to form a sheet, film, etc., processing operations such as an embossing operation are applied to the sheet, etc. Instead of the described processing operation, the absorbent resin may be enveloped into a base material using a thermoplastic resin.

A method of manufacturing an absorbent material by forming an absorbent resin into a sheet or a film is disclosed, for example, in Japanese Unexamined Patent Publication No. 141357/1978 (Tokukaisho 53-141357) and U.S. Pat. No. 4,066,583 wherein a mixture of dried powdery absorbent resin and polyvalent alcohol is sandwiched between fluororesin sheets (base materials), and then a pressure is applied thereto. Japanese Unexamined Patent Application No. 174414/1991 (Tokukaihei 3-174414) and U.S. Pat. No. 5,145,906 disclose absorbent materials produced from dried powdery absorbent resin made of polyacrylic acid (salts) and polysaccharides, etc., and paper diapers as an absorbent article.

Furthermore, Japanese Unexamined Patent Publication No. 230671/1989 (Tokukaihei 1-230671) and U.S. Pat. No. 4,826,880 disclose a method of forming hydrate by adding an aqueous solution in an amount of from 20 percent by weight to 80 percent by weight based on a total amount to dried powdery absorbent resin and immobilizing the dried powdery absorbent resin to a base material by extrusion and dispersion. U.S. Pat. No. 5,428,076 discloses a method of immobilizing dried powdery absorbent resin to a base material to be formed into a sheet.

However, according to the described manufacturing method of Japanese Unexamined Patent Publication No. 141357/1978 (Tokukaisho 53-141357), U.S. Pat. No. 4,066,583, Japanese Unexamined Patent Publication No. 174414/1991 (Tokukaihei 3-174414), and U.S. Pat. No. 5,145,906, the water-containing gel resulting from a polymerization reaction is dried, pulverized and classified to form powdery absorbent resin, and the absorbent resin is formed into a sheet or film by incorporating the absorbent resin with the base material. Therefore, the described methods have a problem in that dust generated when forming the absorbent resin into powders makes the handing of the absorbent resin difficult, and working conditions undesirable. Moreover, the yield of the absorbent resin, and the yield of the resulting molded article are lowered. Besides, complicated processes of manufacturing the absorbent material are required, and the absorbent material cannot be manufactured at low cost.

According to the described conventional manufacturing processes, it is required to reduce an amount of use of the absorbent resin particles to be mixed in the fabric matrix in order to prevent possible gel blocking between absorbent resin particles. Therefore, it is difficult to desirably manufacture an absorbent material having a high content of absorbent resin.

Moreover, the absorbent materials resulting from the conventional methods are inferior in their flexibility, strength, etc. Therefore, such absorbent materials are not tolerable to be taken in a roll, etc., or against tension, and it is not possible to manufacture the absorbent materials continuously. Furthermore, when manufacturing sanitary materials (absorbent articles) such as paper diapers, etc., from the absorbent materials, the resulting sanitary materials are not soft and are uncomfortable to skin of the user.

According to the methods of Japanese Unexamined Patent Publication No. 230671/1989 (Tokukaihei 1-230671), U.S. Pat. No. 4,826,880 and U.S. Pat. No. 5,428,076, after once forming the dried powdery absorbent resin, it is formed into a sheet. Materials such as non-woven fabrics are separately required for maintaining the absorbent resin in a sheet form, and a complicated process of incorporating the material into the absorbent resin powders is required. Besides, dust is generated when forming the absorbent resin into a sheet which causes inconvenience in the handling of the absorbent resin. Moreover, it is likely that the resulting absorbent materials are inferior in flexibility of the sheet, absorbing rate, absorbency under load, and shape retaining property of the sheet which makes the weight of the absorbent resin per unit area small, and desirable absorbing properties cannot be obtained.

The present invention is achieved in a hope of finding a solution to the above-mentioned problems, and accordingly, a main object of the present invention is to provide an absorbent resin and an absorbent material which offer excellent absorbing properties such as absorbing rate, absorbency under load, etc., and a shape retaining property. Another object of the present invention is to provide a method of manufacturing the absorbent material which permits the absorbent material to be manufactured at low cost.

DISCLOSURE OF THE INVENTION

Earnest researches have been made by the inventors of the present invention to achieve the above-mentioned object, and they have found that by reducing the water content of a water-containing gel of a cross-linked polymer under an applied pressure, an absorbent material can be manufactured at low cost, and that the resulting absorbent material includes an absorbent resin which is swollen by absorbing water so as to have anisotropy, and has excellent absorbing properties such as absorbing rate, absorbency under load, shape retaining property, etc., to complete the present invention.

The inventors of the present invention have also found that by applying pressure to, i.e., compressing, a cellular gel of a hydrophilic cross-linked polymer while reducing water content when necessary, absorbent materials can be manufactured at low cost, and the resulting absorbent materials include an absorbent resin which is swollen by absorbing water so as to have anisotropy, and have excellent absorbing properties such as absorbing rate, absorbency under load, shape retaining property, etc.

In order to accomplish the described objects, the absorbent resin of the present invention is characterized by being swollen by absorbing water so as to have anisotropy.

Specifically, in order to accomplish the object of the present invention, an absorbent material of the present invention is characterized by including an absorbent resin, which is formed into a sheet having a flexibility of not more than 1,000 mgf.

In order to accomplish the object of the present invention, a method of manufacturing an absorbent material of the present invention is characterized by reducing a water content of a hydrophilic cross-linked polymer under an applied pressure.

In order to accomplish the object of the present invention, another method of manufacturing an absorbent material of the present invention is characterized by applying a pressure to a cellular gel of a hydrophilic cross-linked polymer while reducing a water content when necessary.

The present invention will describe the present invention in detail.

The absorbent material of the present invention is characterized by having a distorted cross-linked structure and including an absorbent resin (for example, hydrophilic cross-linked polymer particles) which is swollen (anisotropic swelling) by absorbing water. Such absorbent material can be obtained, for example, by (i) a method of reducing a water content of a water-containing gel of a hydrophilic cross-linked polymer under an applied pressure, or (ii) a method of reducing the water content of a cellular gel of a hydrophilic cross-linked polymer under an applied pressure.

In the present invention, the water-containing gel of the hydrophilic cross-linked polymer suggests a gel which is swollen by absorbing aqueous solvent such as water, etc. On the other hand, the cellular gel of the hydrophilic cross-linked polymer suggests a water-containing gel of the hydrophilic cross-linked polymer, which has cells or pores (space) inside.

The cellular gel of the hydrophilic cross-linked polymer can be obtained by introducing foams inside the water-containing gel of the hydrophilic cross-linked polymer. Cells can be introduced inside the water-containing gel of the hydrophilic cross-linked polymer, for example, by boiling the water-containing gel of the hydrophilic cross-linked polymer. However, it is preferable to adopt a method of using a foaming agent when manufacturing the water-containing gel of the hydrophilic cross-linked polymer in view of physical properties. Additionally, the method of manufacturing the water-containing gel and the cellular gel are not particularly limited.

Such water-containing gel of the hydrophilic cross-linked polymer can be obtained with ease by carrying out a polymerization reaction of a monomer component containing, for example, ethylenically unsaturated monomer using an aqueous solvent as a solvent.

The cellular gel of the hydrophilic cross-linked polymer can be obtained with ease by carrying out a polymerization reaction in a presence of a foaming agent using an aqueous solvent as a solvent. For the aqueous solvent, it is not limited to but is preferable to adopt water.

For the ethylenically unsaturated monomer, a water-soluble compound is preferable.

Examples of such ethylenically unsaturated monomer include: unsaturated carboxylic acid such as (meth)acrylic acid, β-acryloyloxypropionic acid, maleic acid, maleic anhydride, fumaric acid, crotonic acid, itaconic acid, or the above acids in a neutralized form (salts), etc.; anionic monomers, such as 2-(meth)acryloylethanesulfonic acid, 2-(meth)acryloyl propanesulfonic acid, 2-(meth)acrylamide-2-methylpropanesulfonic acid, vinyl sulfonic acid, styrene sulfonic acid, and salts thereof, monomers having a nonionic hydrophilic group such as (meth)acrylamide, N-substituted (meth)acrylamide, 2-hydroxyethyl(meth)acrylate, 2-hydroxypropyl(meth)acrylate, methoxypolyethylene glycol(meth)acrylate, polyethylene glycol mono(meth)acrylate, etc.; monomers having an amino group such as N,N-dimethylaminoethyl(meth)acrylate, N,N-dimethylaminopropyl(meth)acrylate, N,N-dimethylaminopropyl(meth)acrylamide, etc., and quaternary salts thereof. Only one kind of the ethylenically unsaturated monomer may be adopted, or two or more kinds thereof may be suitably mixed and adopted.

In consideration of the absorbing properties of the absorbent material among the above-listed ethylenically unsaturated monomers, it is preferable to use a compound of at least one kind selected from the group consisting of (meth)acrylic acids, and neutralized materials thereof (hereinafter referred to as (meth)acrylic acid (salts)), 2-(meth)acryloylethane sulfonic acid (salts), 2-(meth)acrylamide-2-methylpropanesulfonic acid (salts), (meth)acrylamide, methoxypolyethyleneglycol(meth)acrylates, N,N-dimethylaminoethyl(meth)acrylates and quaternary salts of N,N-dimethylaminoethyl(meth)acrylates. A compound of at least one kind containing (meth)acrylic acid (salts) is still more preferable. When the ethylenically unsaturated monomer contains (meth)acrylic acid (salts), it is the most preferable that from 0 mole percent to 90 mole percent of (meth)acrylic acid is neutralized with a basic substance. Furthermore, when the neutralization ratio of (meth)acrylic acid is not more than 50 mole percent, it is preferable that the resulting polymer is neutralized with a basic material in a water containing gel state. Namely, it is preferable that the hydrophilic crosslinked polymer includes cross-linked poly (meth)acrylic acid (salts).

Examples of the basic material include but are not limited to: sodium hydroxide, potassium hydroxide, sodium carbonate, sodium hydrogencarbonate, ammonia, ethanolamine, etc.

The described monomer component may contain other monomer that is copolymerizable with the ethylenically unsaturated monomer (hereinafter referred to as a copolymerizable monomer) to an extent that the hydrophilic characteristics of the hydrophilic crosslinked polymer do not suffer substantially. Examples of such copolymerizable monomer include but are not limited to: (meth)acrylates such as methyl(meth)acrylate, ethyl(meth)acrylate, butyl (meth)acrylate, etc.; hydrophobic monomers such as vinyl acetate, vinyl propionate, etc. Only one kind of the above-listed copolymerizable monomer may be adopted, or two or more kinds thereof may be suitably mixed and adopted.

By carrying out a polymerization reaction of the monomer component using an aqueous solvent, the gel-like hydrophilic polymer, i.e., a non-cellular gel of the present invention can be achieved. On the other hand, in the polymerization reaction, by adopting the foaming agent during a polymerization or after the polymerization, a water-containing gel having cells inside, i.e., the cellular gel of the present invention can be achieved. Hereinafter, the non-cellular gel is simply referred to as a water-containing gel if not specified, and the water-containing gel and the cellular gel are generally referred to simply as gels.

Examples of the foaming agent to be used in the present invention may be but are not limited to: organic solvent such as methyl alcohol, cyclohexane, etc.; carbonates such as sodium (hydrogen)carbonate, ammonium (hydrogen) carbonate, carbonate, potassium (hydrogen)carbonate, magnesium carbonate, carbon dioxide, ethylene carbonate, etc.; water-soluble azo compounds such as 2,2'-azobis(2-methylpropionamizine)dihydrochloride, 2,2'-azobis(2-(2-imidazoline-2-il)propane)dihydrochloride, 2,2'-azobis[2-methyl-N-(2-hydroxyethyl)-propioneamide], etc.; and water uniformly dispersed azo compounds such as 2,2'-azobis(2-methyl propioneamizine)diacrylate, etc. These foaming agents may be solid, liquid or gas at room temperature. From the view point of controlling foaming, a water-soluble polymer or a surfactant may be used in combination.

Although the respective suitable amounts of use of the foaming agent, the water-soluble polymer or the surfactant vary, it is normally based on the total amount of the monomer component, not more than 200 percent by weight, preferably not more than 100 percent by weight in the case of carbonates; not more than 5 percent by weight, preferably not more than 1 percent by weight in the case of the azo compound; not more than 10 percent by weight, preferably not more than 5 percent by weight in the case of the water soluble polymer, and not more than 2 percent by weight and more preferably not more than 1 percent by weight in the case of the surfactant.

When polymerizing the monomer component, the initialization may be effected by a method of adopting a polymerization initiator or a method of adopting an activated energy ray such as radio active ray, an electron beam, an ultraviolet light, or an electromagnetic ray. For the polymerization initiator, for example, radical polymerization initiators may be adopted. Examples of such radical polymerization initiators include but are not limited to: inorganic peroxides such as, potassium persulfate, ammonium persulfate, sodium persulfate, and hydrogen peroxide; organic peroxides such as t-butyl hydroperoxide, benzoyl peroxide, and cumene hydroperoxide; and azo compounds such as 2,2'-azobis (N,N'-dimethylene isobutyl amidine) and salts thereof, 2,2'-azobis(2-amidinopropane) and salts thereof; and 4,4'-azobis-4-cyanovaleric acid, etc. These polymerization initiators may be added at once or several times. Only one kind of the above-listed polymerization initiators may be adopted, or two or more kinds thereof may be suitably mixed and adopted. In the case of employing an oxidative radical polymerization initiator, a redox polymerization may be carried out with a combined use of a reducing agent such as sulfite, bisulfite, L-ascorbic acid, etc.

An amount of use of the polymerization initiators is preferably in a range of from 0.001 percent by weight to 5 percent by weight based on the amount of the monomer component, more preferably in a range of from 0.01 percent by weight to 1 percent by weight. It is not preferable to use the polymerization initiators in an amount less than 0.001 percent by weight, as effects of adopting the polymerization initiators would be poor. It is also not preferable to use the polymerization initiator in an amount exceeding 5 percent by weight, as improved effects cannot be expected from the effects achieved when adopting the polymerization initiators in the described range. Moreover, an average molecular weight of the resulting hydrophilic crosslinked polymer is reduced, which causes inferior shape retaining property. Here, the method of polymerizing (a) monomer component (s) is not particularly limited.

In order to obtain an absorbent material having desirable absorbing properties, it is preferable that the hydrophilic crosslinked polymer is inner portion cross-linked by a reaction or a copolymerization reaction with a cross-linking agent having a plurality of polymerizable unsaturated groups and/or a plurality of reactive groups. Namely, the resulting hydrophilic crosslinked polymer having a three-dimensional net structure offers shape retaining property. The hydrophilic crosslinked polymer may be of self-cross-linkable type which does not require a cross-linking agent; however, it is preferable to adopt a cross-linking agent.

The cross-linking agent is not particularly limited, and any compound that is reactive with an ethylenically unsaturated monomer or a polymer thereof may be used. Examples of such cross-linking agent include: tetraallyloxy ethane N,N'-methylene bis(meth)acrylamides, (poly) ethylene glycol di (meth)acrylates, glycerol tri(meth) acrylates, trimethylol propane tri(meth)acrylates, triallyl amine, triallyl cyanurate, triallyl isocyanurate, glycidyl (meth)acrylate, (poly)ethylene glycol, diethylene glycol, (poly)glycerol, propylene glycol, diethanol amine, trimethylol propane, pentaerythritol, (poly)ethylene glycol diglycidyl ether, (poly)glycerol polyglycidyl ether, epichlorohydrin, ethylenediamine, polyethyleneimine, (poly)aluminum chloride, aluminum sulfate, potassium chloride, and magnesium sulfate, etc. In consideration of its reactivity, during or after the polymerization reaction, only one kind of the above-listed cross-linking agents may be adopted, or two or more kinds thereof may be suitably mixed and adopted. Among the above-listed cross-linking agents, it is preferable to adopt a cross-linking agent having a plurality of polymerizable groups, and among them, it is more preferable to adopt a mixture of the cross-linking agent of at least one kind selected from the group consisting of triallylamine, tetraallyloxy ethane, N,N'-methylenebis (meth)acrylamides, (poly)ethylene glycol di(meth)acrylates, and trimethylol propane tri(meth)acrylate and a monomer component.

The amount of use of the cross-linking agent is generally in a range of from 0.001 mole percent to 2 mole percent, preferably from 0.01 mole percent to 1 mole percent, based on the amount of the monomer component. It is not preferable to-use the cross-linking agent in an amount less than 0.001 mole percent, as the gel collapses when being compressed irrespectively of whether or not the gel contains foams, and may not have desirable absorbing properties. It is also not preferable to use the cross-linking agent in an amount above 2 mole percent, irrespectively of whether or not the gel contains foams, as it is difficult to decompress the gel, and the resulting absorbent material may not have desirable absorbing properties.

Furthermore, the monomer component may be polymerized in a presence of a hydrophilic polymer such as starch, cellulose, chitin, polyvinyl alcohol, polyacrylic acid (salts), and crosslinked polymers thereof, polyethylene glycol, etc. As a result, a reaction of forming a graft bond, a complex, is carried out simultaneously when carrying out the polymerization reaction of a monomer. Namely, a hydrophilic crosslinked polymer having a graft bond, a complex, etc., between the polymer of a monomer component and the hydrophilic polymer.

The method of polymerizing the monomer component is not particularly limited, and known polymerization methods such as a solution polymerization or reversed-phase suspension polymerization may be adopted. Examples of such solution polymerizations include but are not limited to: a solution polymerization method in which an aqueous solution of monomer components are placed in a predetermined mold; a solution polymerization method in which a mixer such as a kneader, etc., equipped with a mixing blade of a predetermined shape is used as a polymerization device, and the resulting hydrophilic polymer gel is pulverized by a shear stress of the mixing blade, etc. Between the described polymerization methods, the latter method is more preferable as a granular gel can be obtained.

When polymerizing the monomer components by aqueous solution polymerization, the solution of the monomer component may or may not be stirred. However, when carrying out a polymerization reaction in a presence of a foaming agent, it is preferable that the aqueous solution of the monomer component be let still for at least a predetermined time during the reaction to achieve an effective forming by a foaming agent. Specifically, by leaving the aqueous solution of the monomer component still for a predetermined time from a start of polymerization reaction till a point a polymerization rate becomes 10 percent, more preferably 30 percent, still more preferably 50 percent, and the most preferably till the completion of the reaction, a still improved foaming effect by the foaming agent can be achieved. The time from the dispersion of the foaming agent till the start of the polymerization reaction of the monomer component is not particularly limited. However, the shorter the time, the more preferable it is.

When the gel of the hydrophilic cross-linked polymer resulting from the aqueous polymerization method is in a form of a bulk, it is preferable to pulverize the gel into particles having a predetermined diameter. The method of pulverizing the gel in a particular form is not particularly limited, and known pulverization methods of applying a shear stress to the gel may be adopted. Examples of the device of applying such shear stress include but are not limited to: screw type extruding devices like a meat chopper, various cutters, a (mechanical pressurizing) kneader, an internal mixer, a Banbury mixer, and other similar kneaders.

As an example of the reversed-phase suspension polymerization method, for example, a method of performing a polymerization by suspending a solution of a monomer component in the presence of a dispersant in a hydrophobic organic solution may be adopted. The described reversed-phase suspension polymerization enables a water-containing gel that is spherical (particular) in shape or a cellular gel to be obtained without pulverization upon completion of the polymerization reaction.

The hydrophilic crosslinked polymer is swollen by absorbing an aqueous solvent, and when the ratio of the aqueous solvent based on a total amount of hydrophilic crosslinked polymer and the aqueous solvent (hereinafter referred to as a water content) becomes not less than around 30 percent by weight, the hydrophilic crosslinked polymer is gelled. Namely, the water-containing gel of the hydrophilic crosslinked polymer and the cellular gel of the hydrophilic crosslinked polymer generally have a water content of not less than around 30 percent by weight, preferably from 30 percent by weight to 90 percent by weight and still more preferably from 40 percent by weight to 80 percent by weight. The water content may be adjusted based on the monomer density before or after polymerization when an occasion demands, or may be adjusted by a drying treatment or post addition of the aqueous solvent.

When the water content is less than around 30 percent by weight, as the hydrophilic crosslinked polymer is not formed into the gel, it is difficult to calendar the hydrophilic crosslinked polymer. Namely, in the case of adopting the rigid hydrophilic crosslinked polymer, when calendaring the cross-linked absorbent polymer, it is difficult to sufficiently compress the absorbent resin, i.e., each particle of the hydrophilic crosslinked polymer, to have a flat shape.

On the other hand, when the water content is above 90 percent by weight, irrespectively of whether or not the gel contains cells, the convenience in handing the gel is lowered, and moreover, it is difficult to calendar the gel. In such case, the gel strength becomes poor, and when compressing by reducing the water content, particles of the hydrophilic crosslinked polymer are not distorted but simply collapse. Therefore, it may not be possible to retain the original shape of the absorbent resin by absorbing water. Namely, it becomes difficult to ensure a desirable shape retaining property. Therefore, such condition is unpreferable as the desirable absorbing rate, and the absorbency under load may not be achieved. In the present invention, the shape retaining property indicates that the hydrophilic crosslinked polymer particles (absorbent resin) are immobilized in a distorted state, and when swollen by absorbing water, the polymer particles are retained to an original state before a pressure was applied thereto (compression) by being swollen in a non-similar shape.

Here, it is obvious that the absorbent resin is swollen (anisotropically swells) into a non-similar shape from a comparison between the shape of the absorbent resin after compression and the shape of the absorbent resin after being swollen by absorbing water.

The described gel of the hydrophilic crosslinked polymer further absorbs water; body fluids such as urine, sweat, blood; an aqueous liquid such as drip (juice) exuded from meats, fishes, vegetables, fruits; etc. When contacting the aqueous fluids, the gel is swollen by absorbing the aqueous fluids, which causes a further volume expansion. It is preferable that the gel of the hydrophilic crosslinked polymer is capable of absorbing the aqueous fluid of not less than three times of the dead weight (weight of the gel).

Further, the cellular gel of the hydrophilic crosslinked polymer shows a volume swell of from 1.01 to 10 times of the non-cellular water-containing gel, preferably from 1.05 to 5 times, and more preferably from 1.1 to 3 times. By adopting the cellular gel of the hydrophilic crosslinked polymer, an absorbent resin which shows excellent absorbing properties can be obtained.

It is further preferable to adopt a porous gel as the cellular gel in the present invention. When polymerizing the monomer component in the presence of the foaming agent, the foaming agent dissolved in the monomer solution is foamed by vaporization, decomposition, deposition or volume swell, etc., and cells (space) are formed in the resulting polymer (gel-like hydrophilic crosslinked polymer). As a result, the porous gel (cellular gel) containing many foams inside can be obtained.

In the present invention, porous indicates that the gel contains per 1 $cm^3$ of the gel (cellular gel) at least 10 cells, preferably not less than 100 cells, more preferably not less than 1,000 cells, and still more preferably not less than 10,000 cells. Here, whether the cells are continuous or independent does not matter.

When the number of cells is less than 10, or the volume swell is less than 1.01, the gel of the hydrophilic crosslinked polymer may not offer sufficient effects of improving the absorbing rate or permeability to liquid. On the other hand, when the number of cells exceeds 1,000,000 or the volume swell exceeds 10 times the non-cellular water-containing gel, the volume efficiency of the manufacturing device is lowered, and the cost is increased, and further it becomes difficult to restore the compression.

The porosity diameter of the cellular gel can be obtained by the analysis of an image of the cross-section of the cellular gel by an optical microphotograph. Namely, by preparing a histogram showing a distribution of the porosity diameter of the cellular gel by an image analysis, and computing an average number of holes based on the histogram, an average porosity diameter is computed. In this case, the magnification of the optical microphotograph is not particularly limited; however, it is preferably in a range of from 10 times to 1,000 times, and still more preferably in a range of from 20 times to 100 times.

In consideration of the absorbing rate and the permeability to aqueous liquid, the average porosity diameter of the cellular gel is generally in a range of from 1 $\mu$m to 1,000 $\mu$m, preferably in a range of from 10 $\mu$m to 300 $\mu$m, and more preferably in a range of from 20 $\mu$m to 200 $\mu$m. By adjusting the porosity diameter of the cellular gel within the described range, an absorbent material which shows excellent absorbing rate and permeability to aqueous liquid can be obtained.

Furthermore, as the cellular gel is porous having an average porosity diameter in the described range, a sufficient space for passing the aqueous liquid inside the cellular gel, i.e., the absorbent resin, can be ensured both without an applied pressure and under an applied pressure. Therefore, the cellular gel shows excellent permeability to aqueous liquid and dispersibility and improved absorbing rate and water retention characteristics can be achieved by the capillarity.

It is preferable that the water-containing gel and the cellular gel of the present invention are in a granular form. Namely, the respective shapes of the particles, i.e., the absorbent resin when absorbing water are not particularly limited, and may be formed into cubic, polyhedron, spherical, disk, sector, stick-like, needle, fabric, flake or undefined (irregular) shape, etc. The water-containing gel or the cellular gel may be primary particles or agglomerates (secondary particles) in which primary particles agglomerate. Among these shapes, those of irregular shapes obtained in the process of pulverizing in which particles diameters are not uniform, or spherical shape obtained by a reverse phase suspension polymerization are especially preferable.

The described water-containing gel and the cellular gel have a wide particle size distribution; however, it is preferable to have a predetermined range of particle size distribution and a predetermined average particle diameter. It is preferable that the average particle diameter of the resulting water-containing gel and the cellular gel dried, i.e., the average particle diameter of the hydrophilic crosslinked polymer resulting from respective polymerization reactions (hereinafter, referred to as a dried average particle diameter) be in a range of from 50 $\mu$m to 2,000 $\mu$m, more preferably in a range of from 60 $\mu$m to 1,500 $\mu$m, still more preferably in a range of from 80 $\mu$m to 1,000 $\mu$m, and most preferably in a range of from 100 $\mu$m to 600 $\mu$m.

In order to achieve an absorbent material and an absorbent article which are soft and comfortable to use and convenient to handle, it is preferable that the water-containing gel and the cellular gel do not substantially contain particles having a particle diameter of not less than 5 mm, and more preferably do not substantially contain particles having a particle diameter of not less than 3 mm.

The gel having a dried average diameter of above 2,000 $\mu$m is inferior in its handling, surface smoothness, and moreover, a surface area per unit weight of the gel is relatively small although the gel has foams irrespectively of whether or not the gel is cellular. Therefore, it is not preferable as the absorbing rate of the resulting absorbent material is low. Moreover, it is not preferable to adopt the gel having a dried average particle diameter of less than 50 $\mu$m, irrespectively of whether or not the gel contains foams, as the convenience in handling the gel and the permeability to aqueous liquid suffer.

The dried average particle diameter can be converted after classifying the gel in the following manner. Namely, first, the beaker of a predetermined size (container) is placed on a magnetic stirrer, and 1,200 g of an aqueous solution of 20 percent by weight of sodium chloride is placed therein. Then, after placing 25 g of the target gel having a solid portion of $\alpha$ percent by weight, the gel is dispersed by rotating the rotator at 300 rpm. After stirring it for 60 minutes, the dispersed solution is poured into six sieves stacked in the order of the sieve openings (from the top sieve). Here, the respective sieve openings are selected to be $r_1$=0.075 mm, $r_2$=0.30 mm, $r_3$=0.60 mm, $r_4$=0.85 mm, $r_5$=2.0 mm, and $r_6$=9.5 mm from the bottom. Then, 6,000 g of 20 percent by weight of sodium chloride are poured gently from the top, thereby classifying the gel.

After fully rinsing off the gel thus classified, the weight of the water-containing gel is measured. Here, the sum of the weight of respective gels, i.e., the total weight of the gels thus classified and rinsed off is determined to be W(g). Then, according to the following formula $R_n=[(\alpha/100)\cdot(25/W)]^{1/3} \times r_n$, the opening $r_n$ is converted into the opening $R_n$ (mm) in which the dried gel is classified. The weight (percent by weight) of the gel remaining on each sieve with respect to the total weight W is measured.

Then, each respective ratio of the gel remaining on the sieve $R_n$ to the gel remaining on the sieve respectively having an opening of $R_n$ ($R_1$, $R_2$, $R_3$, $R_4$, $R_5$, $R_6$) is plotted on an algorithmic probability paper. From the plotted graph, the opening R at which the ratio of the weight of the gel with respect to the total weight W is 50 percent is read, and this opening R is determined to be an average particle diameter (mm) of the dried gel, thereby obtaining the dried average particle diameter.

It is further preferable that the water-containing gel and the cellular gel respectively have a water-soluble component of not more than 20 percent by weight, preferably in a range of from 0.1 percent by weight to 20 percent by weight, and still more preferably in a range of from 1 percent by weight to 15 percent by weight. It is not preferable to select the content of the water-soluble component to be above 20 percent by weight, as sufficient gel strength cannot be achieved. On the other hand, if the content of the water-soluble component is less than 0.1 percent by weight, the absorbency and the absorbing rate of the absorbent material become insufficient.

It is further preferable that the conversion of the gel falls in a range of from 90 percent to 99.99 percent irrespectively of whether nor not the gel contains foams. If the polymerization rate of the gel is less than 90 percent, the properties will be degraded as the water content is reduced, and the described shape retaining property may not be ensured.

In the present invention, by specifying the water content or the water-soluble component content of the gel, the kind of the main chain of the hydrophilic cross-linked polymer, the average particle diameter or the dried average particle diameter of the gel, a still improved shape retaining property can be obtained.

When preparing the absorbent material in accordance with the present invention, it is preferable that these gels (water-containing gel, the cellular gel) further contain polyhydric alcohol. Examples of such polyhydric alcohol include but are not limited to: ethylene glycol, diethylene glycol, polyethylene glycol, triethylene glycol, tetraethylene glycol, polyethylene glycol, 1,3-propanediol, dipropylene glycol,2, 2,4-trimethyl-1,3-pentanediol, polypropylene glycol, glycerol, polyglycerol, 2-butene-1,4-diol, 1,4-butane diol, 1,5-pentane-diol, 1,6-hexanediol, 1,2-cyclohexane dimethanol, 1,2-cyclo-hexanol, trimethylolpropane, diethanolamine, triethanol amine, polyoxy propylene, oxyethylene-oxypropylene block copolymer, pentaerythritol, sorbitol, polyvinyl alcohol, glucose, mannitol, sucrose, dextrose, etc. Only one kind of the above-listed polyhydric alcohol may be adopted, or two or more kinds thereof may be suitably mixed and adopted. Among the above-listed polyhydric alcohol, glycerol is the most preferable.

The gel including polyhydric alcohol offers an absorbent material that can be formed into a sheet with ease and shows excellent flexibility, strength and cushioning characteristics. When the absorbent material contacts water, the absorbent resin, i.e., the hydrophilic crosslinked polymer particles can be restored into an original shape before having a pressure applied thereto. Namely, an improved shape retaining property can be achieved.

The (total) amount (hereinafter referred to as a total amount) of the polyhydric alcohol with respect to a total amount of a solid portion and a polyhydric alcohol portion of the gel (water-containing gel or the cellular gel) is preferably in a range of from 0.1 percent by weight to 80 percent by weight, more preferably in a range of from 1 percent by weight to 60 percent by weight, and still more preferably in a range of from 5 percent by weight to 30 percent by weight. By using the polyhydric alcohol in the described range, a gel can be formed into a sheet with ease, and the gel can be easily pulverized. Moreover, the flexibility and the strength of the absorbent material (tensile strength, tearing strength) are improved. It is not preferable to set the ratio of the polyhydric alcohol based on a total amount to be less than 0.1 percent by weight, because the effect achieved by adopting the polyhydric alcohol is small, and a sufficient strength cannot be applied to the absorbent material. On the other hand, it is also not preferable to set the ratio of the polyhydric alcohol to larger than 80 percent by weight with respect to the total amount, as too much polyvalent alcohol is used, which causes the absorbent material to be sticky and lowers various absorbing properties of the absorbent material. In the present invention, the method of mixing the gel of the hydrophilic crosslinked polymer and the polyhydric alcohol, i.e., the method of preparing a mixture of the water-containing gel or the cellular gel with polyvalent alcohol (hereinafter simply referred to as a mixture) is not particularly limited.

When pressurizing the hydrophilic crosslinked polymer gel, the hydrophilic crosslinked polymer may be surface-crosslinked (secondary crosslinkage) by further adding a surface cross-linking agent. The surface cross-linking agent is not particularly limited, and any known surface cross-linking agent of a compound having a plurality of reactive groups and which is reactive to a functional group such as a carboxyl group of the hydrophilic crosslinked polymer may be used.

Examples of such surface cross-linking agent include but are not limited to: polyhydric alcohol such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymer, pentaerythritol, sorbitol, polyvinyl alcohol, glucose, mannitol, sucrose, dextrose, etc.; polyhydric epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, etc.; polyhydric amine compounds such as ethylenediamine, diethylenetriamine, triethylenetetramine, tetraethylenepentamine, pentaethylenehexamine, polyethyleneimine, etc.; polyhydric isocyanate compounds such as 2,4-tolylene diisocyanate, hexamethylene diisocyanate, etc.; polyhydric oxazoline compounds such as 1,2-ethylene bisoxazoline, etc.; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxopane-2-one, etc.; haloepoxy compounds such as epichlorohydrin, epibromohydrin, α-methylepichlorohydrin, etc.; polyvalent metallic compounds such as hydroxides and chlorides of metals: zinc, calcium, magnesium, aluminum, iron, zirconium, etc. Only one kind of the above-listed surface cross-linking agent may be adopted, or two or more kinds thereof may be suitably mixed and adopted. Among the above-listed surface cross-linking agents, polyvalent epoxy compound is preferable.

As described, by surface cross-linking the hydrophilic polymer using the surface cross-linking agent, the shape retaining property, and the absorbency under pressure of the absorbent material are still improved. Moreover, the dispersibility of the aqueous liquid and various absorbing properties such as permeability, etc., when absorbing the aqueous liquid can be improved. Furthermore, when contacting the aqueous liquid, a component to be eluted in the aqueous liquid, i.e., an amount of the water-soluble component can be reduced.

The amount of use of the surface cross-linking agent may be suitably selected according to the kind of the surface cross-linking agent, a combination thereof, a degree of surface cross-linkage, etc. However, an amount of use of the surface cross-linking agent is generally in a range of from 0 to 10 percent by weight, preferably in a range of from 0.001 percent by weight to 5 percent by weight, and still more preferably in a range of from 0.01 percent by weight to 1 percent by weight.

Additionally, a mixture of the water-containing gel, the cellular gel, a mixture of each gel and polyhydric alcohol and a surface cross-linking agent is not particularly limited. When applying a pressure to the gel, by applying pressure and at the same time heat, a crosslinkable reaction of the hydrophilic cross-linked polymer and the surface cross-linking agent can be further accelerated.

When applying a pressure to the gel, preferably when calendaring the gel, if necessary, an auxiliary molding compound may be used. Namely, the absorbent material may include an auxiliary molding compound other than gel and polyhydric alcohol. As the molding compound, a surface active agent, fibers, various fine water-insoluble particles, etc., may be used. Such auxiliary molding compounds may be used alone or in combination. When forming the absorbent material into a sheet, it is preferable that the absorbent material contains fibers.

The described surface active agent includes anionic surface active agents, nonionic surface active agents, cationic surface active agents, and amphoteric ionic surface active agents. Examples of anionic surface active agents include but are not limited to: fatty acid salts of sodium oleate, potassium castor oil, etc., alkylsulfuric ester salts of lauryl sodium sulfide, lauryl ammonium sulfide, etc., alkylbenzene sulfonic acid salts such as dodecyl benzene sodium sulfonic acid salts, etc., alkyl naphthalene sulfonic acid salts, dialkyl sulfo-succinate, alkyl phosphate salts, and naphthalene-sulfonic formalized condensation product, and polyoxyethylene alkyl sulfate salts, or the like.

Examples of the nonionic surface active agent include but are not limited to: polyoxyethylene alkyl ether, polyoxyethylene alkyl phenol ether, polyoxyethylene fatty acid ester, sorbitan fatty acid ester, polyoxyethylene sorbitan fatty acid ester, polyoxyethylene alkylamine, and an oxyethylene-oxypropylene block copolymer.

Examples of the cationic surface active agent include but are not limited to: alkyl amine salts such as lauryl amine acetate, stearyl amine acetate, etc., quaternary ammonium salts such as lauryl trimethyl ammonium chloride, stearyl trimethyl ammonium chloride, or the like.

Examples of the amphoteric ionic surface active agent include but are not limited to: lauryl dimethylamine oxide. Only one kind of the above-listed surface active agents may be adopted, or two or more kinds thereof may be suitably mixed and adopted. By adopting the surface active agent, the resulting mixture can be calendared to be formed into a sheet still more easily.

For the described fibers, both long fiber and short fiber may be adopted. Examples of such fiber include but are not limited to: wood fibers such as pulp, etc., natural fibers such as hemp, etc., polyester, inorganic fibers such as a glass fiber, etc. Examples of polyester include but are not limited to polyethylene terephthalate (PET), etc. Only one kind of the above-listed fibers may be adopted, or two or more kinds thereof may be suitably mixed and adopted. Among the above-listed fibers, synthetic fibers are preferable and hydrophobic synthetic fibers are still more preferable. Besides, paper (Japanese paper) made from these fibers, thread, woven or non-woven cloth, etc., may be adopted. By adopting the fiber, a still improved absorbing rate of the resulting absorbent material can be obtained, and a still improved shape retaining property can be achieved. Furthermore, when forming the absorbent material into a sheet, the sheet can be made thin uniformly (for example, several mm, etc.,). When kneading the water-containing gel, the cellular gel or a mixture of each gel and polyhydric alcohol with the fibers by the kneader, it is preferable to adopt short fibers of from 2 mm to 50 mm length, preferably from 10 mm to 40 mm length, and still more preferably from 20 mm to 30 mm length so as to prevent a mixing blade of the kneader from being caught by fibers.

Examples of minute particles include but are not limited to: mica, pyrophyllite, kaolinite, hulsite, and inorganic material similar to clayish minerals, and silica (silicon dioxide) having an average particle diameter of not more than 50 $\mu$m, such as Aerosil 200 (available from Japan Aerosil Ltd.), Carplex #80 (available from Shionogi & Co., Ltd.) may be cited; carbon black, activated carbon, etc. Only one kind of the above-listed minute particles may be adopted, or two or more kinds thereof may be suitably mixed and adopted.

The amount of use of the auxiliaries is not particularly limited, and may be suitably adjusted in consideration of the kind or combination, etc., thereof. The total amount of the auxiliaries is generally in a range of from 0.01 to 100 parts by weight, desirably from 0.1 to 50 parts by weight, and more desirably from 0.1 to 30 parts by weight, based on 100 parts by weight of the solid portion of the gel (i.e., hydrophilic crosslinked polymer). When the auxiliaries are used in an amount above 100 parts by weight, the resulting absorbent material is likely to be hardened. The method of mixing the water containing gel, the cellular gel, or a mixture of each gel and the polyhydric alcohol and the mixing conditions are not particularly limited.

According to the present invention, by reducing the water content of the water-containing gel under an applied pressure, an absorbent material (I) containing a non-cellular gel which is swollen by absorbing water so as to have anisotropy can be obtained. The present invention also permits the absorbent material (II) containing a porous absorbent resin which is swollen by absorbing water so as to have anisotropy to be obtained by pressurizing the cellular gel while reducing water content if necessary. In the present invention, when adopting the gel having foams inside, i.e., the cellular gel, as the gel, depending on the water content, it is not necessary to always apply pressure and reduce water content at the same time. However, in order to optimize the effect of the shape retaining property, it is preferable to apply pressure while reducing the water content even when adopting the cellular gel as the gel. As the absorbent resin is formed into a shape before having applied pressure (compression) by the anisotropic expansion of the absorbent resin in a non-similar shape, an absorbent material ((absorbent material (I) or absorbent material (II)) which has still improved absorbing properties such as absorbing rate, absorbency under load and shape retaining property can be obtained.

The method of pressurizing the gel is not particularly limited, and the known method may be adopted. For the pressurizers to be adopted in the present invention, a device of reducing the water content from the gel under an applied pressure (amount of aqueous solvent) is preferable, and a device of molding into a sheet by calendaring is preferable. The described pressurizers include but are not limited to a drum dryer, etc., provided with a combination of a compressor. When pressurizing the gel, by compression forming the absorbent material (absorbent material (I) or absorbent material (II)) by reducing the water content of the gel while applying pressure, an absorbent material for retaining the original shape before having an applied pressure can be obtained.

Examples of the method of reducing water content include but are not limited to (i) a method of reducing a water content by reducing pressure at a temperature below room temperature while compressing the gel; (ii) a method of removing water by immersing the gel in a hydrophilic organic solvent under an applied pressure; and (iii) a method of heating the gel under an applied pressure, etc., and among the above-listed three method, the method (iii) is the most preferable.

In this case, examples of the heating method include but are not limited to: 1̂ a heating method of a conductive heat transfer type for heating of a gel by making the gel in direct contact with a heating surface of the heater; 2̂ a heating method of a hot air heat transfer type by a hot air or steam, etc.; 3̂ a radiant heating method of a transfer-type by radiation such as an infrared ray, an extreme infrared ray, etc., 4̂ dielectric heating by microwaves, etc. These methods can be selectively used. Among all, 1̂ a heating method of conductive heat transfer system by a heat plate, heat drum, a heat roller, a heat belt, etc., is preferable. It is especially preferable to adopt a method of applying heat and pressure to a heating surface of the absorbent material (absorbent material (I) or the absorbent material (II)), i.e., a heating surface of the gel by combined use of a plate, a drum, a roller, a belt, etc.

When adopting the method 1̂, it may be arranged so as to generate a distortion in the cross-linked structure of the absorbent resin by applying heat and pressure to the heating face of the gel so that a temperature difference occurs, for example, between the heating surface (first face) that is a contact face with the heater and the back surface, i.e., an opposite surface (second surface) to the first surface in a gel thickness direction to generate a distortion in the cross-linked structure of the absorbent resin. When obtaining a sheet-like absorbent material (I)•(II) (sheet) by the above method, as the shape retaining property of the absorbent resin (shape retaining property) of the absorbent resin differs between the first face (namely, heating surface) and the second face (for example, non-heating surface or low temperature surface) of the sheet, the sheet can be curled so as to have a curvature to have a low temperature region inside. The sheet absorbs physiologic saline solution from 1 to 50 times, preferably from 2 to 25 times, and more preferably from 5 to 20 times by weight of the hydrophilic crosslinked polymer, so that both ends of the sheet can be curled. This phenomenon occurs irrespectively of the size of the sheet. However, the phenomenon can be observed with ease by making a from 1 cm to 10 cm sheet be swollen by absorbing water.

Next, referring to FIG. 1, a method of pressurizing a gel (gel composition) by adopting a drum dryer provided with a compressor as one example of a calendaring method will be explained in reference to FIG. 1. The pressurizing method of the gel is not limited to the method of adopting the drum dryer provided with the compressor.

The drum dryer is, for example, an open-type single drum dryer, and as shown in FIG. 1, the drum dryer (single drum dryer) provided with the compressor includes a drum dryer 1, a pressurizing roller 2 as a compressor, a scraper 3, and a driving unit (not shown), etc. The drum dryer 1 is made of stainless, etc., and is rotatably driven in a direction shown by an arrow A at number of rotations of, for example, not more than several rpm. In the dryer drum 1, a heater (not shown) is stored so as to permit the surface of the drum dryer 1 to be heated to a predetermined temperature.

The pressurizing roller 2 is made of a stainless, etc., and a predetermined interval is formed from the surface of the drum dryer 1. Namely, a predetermined clearance is formed between the pressurizing roller 2 and the surface of the drum dryer 1. The pressurizing roller 2 is rotatably driven in a direction of an arrow B at a predetermined number of rotations with respect to the number of rotations of the drum dryer 1. Then, the pressurizing roller 2 is able to apply a predetermined pressure with respect to a gel composition 10 (to be described later) as a mixture that is fed on the surface of the drum dryer 1. Namely, the drum dryer 1 is capable of reducing the water content of the gel while applying pressure to a gel composition 10.

The scraper 3 is formed so as to be in contact with the surface of the dryer drum 1, and a sheet 11 (to be described layer) adhering to the surface is scraped off. On the surface of the drum dryer 1 and the surface of the pressure roller, mirrors are formed. In the pressurizing roller 2, a heater may be stored so as to heat the surface of the pressurizing roller 2 to a predetermined temperature.

In the described arrangement, on the upstream side of the pressurizing roller 2 attached to the drum dryer 1, a gel composition 10 composed of the gel (water-containing gel or cellular gel), polyhydric alcohol and, if necessary, a subsidiary foaming material are fed. The gel composition 10 adhering to the surface of the drum dryer 1 is transported in the direction of an arrow A, to reach a clearance between the drum dryer 1 and the pressurizing roller 2.

Then, by the pressurizing roller 2, the gel composition 10 is pressurized (calendared) to reduce the thickness to not more than 15 percent, preferably not more than 10 percent and still more preferably not more than 5 percent of the original thickness to form a sheet 11. Then, the sheet 11 being transported in the direction of an arrow A adhering to the surface of the drum dryer 1 is heated by the above heater via the surface of the drum dryer 1. The temperature of the surface of the drum dryer 1, i.e., the heating temperature of the gel composition 10 is preferably in a range of from room temperature to 300° C., more preferably in a range of from 50° C. to 200° C., and still more preferably in a range of from 100° C. and 180° C. It is not preferable to set the heating temperature above 300° C., as the hydrophilic crosslinked polymer and the polyvalent alcohol decompose. By applying heat to the sheet 11, namely, by heating the gel contained in the gel composition 10, the water content (amount of aqueous solvent) is reduced. Namely, with an application of heat, a part of polyhydric alcohol may be evaporated.

The reduction ratio of the aqueous solvent in the gel is not particularly limited. Although the reduction ratio differs depending on whether or not the gel contains foams, it is preferably in a range of from 10 percent by weight to 90 percent by weight, and more preferably in a range of from 40 percent by weight to 80 percent by weight based on the amount of the aqueous solvent before applying pressure.

When the gel composition 10 is not heated, i.e., when the temperature on the surface of the drum dryer 1 is at room temperature, the ratio of reduction in water content is substantially 0 percent by weight. If the ratio of reduction in water content is small, it is difficult to obtain the desirable shape retaining property. Additionally, when reducing the water completely (the gel having a water content of 0%), it is likely that various properties and flexibility are degraded.

When pressurizing the gel composition 10, in order to obtain a desirable shape retaining property, it is preferable to pressurize the gel so as not to be subdivided (collapse). For this reason, it is preferable that the gel (water-containing gel, cellular gel) is sub-divided to have the described fine particle diameters beforehand.

After being transported in a direction of an arrow A, the sheet 11 is scraped off from the surface of the drum dryer 1 by the scraper 3. The sheet 11 thus scraped off, i.e., the absorbent material is wound around a roll, etc., (not shown) when the need arises. Additionally, as the absorbent material has an appropriate flexibility or strength by including the polyhydric alcohol, it would not be broken by being bent, for example, at 90° or further at 180° when being removed by the scraper 3. Alternatively, the sheet 11 may be separated from the surface of the drum dryer 1 by applying an appropriate tension to the absorbent material. As a result, a sheet-like absorbent material (absorbent material (I) or absorbent material (II)) having at least one smooth surface can be obtained.

As described, according to the present invention, by reducing the water content while applying pressure to the water-containing gel, the absorbent material (I) having an excellent water absorbing rate and absorbency under load can be obtained. As described, in the present invention, by applying a pressure to the cellular gel, preferably by applying pressure while reducing water, the absorbent material (II) which is superior to the absorbent material (I) in its absorbing rate and absorbency under load can be obtained.

Generally, after obtaining a powdery absorbent material, when forming, for example, a sheet-like powdery absorbent material, the absorbing rate and absorbency under load of the resulting absorbent material are significantly lowered by comparing with the pre-formed absorbent material. For this reason, it is difficult to prepare an absorbent material having excellent absorbency under load and absorbing rate suited for use in molding articles by the conventional method. However, according to the present invention, it is permitted to directly form (into a sheet) from the water-containing gel or cellular gel, thereby obtaining a molded article of high value (for example, sheet-like absorbent materials (I) and (II)).

According to the present invention, the absorbing rate of the absorbent material (I) as a molding article (sheet) adopting the water containing gel is not more than 150 seconds, and with a combined use of the surface cross-linking agent, or by specifying the water content, water-soluble component in the water-containing gel, the kind of a main chain of the hydrophilic crosslinked polymer, the average particle diameter or the dried average particle diameter of the water-containing gel, a high absorbing rate of not more than 100 seconds, more preferably not more than 50 seconds and still more preferably not more than 30 seconds can be achieved. However, it is not preferable to set the absorbing rate to be not more than 1 second, particularly not more than 0.5 seconds, as the absorbing rate is too low which causes the liquid diffusivity to be lowered.

In the present invention, the absorbing rate of the absorbent material (I) as a molding (sheet) in the case of adopting water-containing gel as the gel, particularly, the absorbing rate under applied pressure is not less than 15 g/g, and with a combined use of the surface cross-linking agent, the water content and water-soluble content in the water-containing gel, the kind of a main chain of the hydrophilic polymer, the average particle diameter, or the dried average particle diameter, etc., of the water-containing gel, an absorbency of preferably not less than 20 g/g and more preferably not less than 25 g/g can be obtained.

On the other hand, in the present invention, absorbing rate of the absorbent material (II) as a molding (sheet) in the case of adopting cellular gel as the gel is not more than 150 seconds, and with a combined use of the surface cross-linking agent, or by specifying the amount of water or the water-soluble component in the cellular gel, the porosity diameter, or number of foams in unit volume, the kind of main chains of the hydrophilic crosslinked polymer, the average particle diameter, or the dried average diameter of cellular gel, the absorbing rate can be set to not more than 100 seconds, more preferably not more than 50 seconds, and still more preferably not more than 30 seconds, and the most preferably not more than 20 seconds. However, when the absorbing rate is not more than 1 second, particularly not more than 0.5 seconds, the absorbing rate is too high which causes the liquid diffusivity to be lowered.

In the present invention, in the case of adopting cellular gel as the gel, the absorbency of the absorbent material (II) as a molding (sheet), particularly the absorbency under applied pressure is not less than 15 g/g, and with a combined use of the surface cross-linking agent or by specifying the water content or the water-soluble content in the cellular gel, the porosity diameter, or the number of foams in the unit volume, the kind of a main chain of the hydrophilic crosslinked polymer, the average particle diameter or the dried average particle diameter of the cellular gel, an absorbency of not less than 20 g/g, more preferably not less than 25 g/g, and more preferably not less than 30 g/g can be obtained. As described, by adopting the cellular gel as the gel, an absorbent material (II), for example, formed into a sheet having excellent absorbing properties can be obtained such as an absorbing rate of not more than 20 seconds and an absorbency under load of not more than 30 g/g.

Conventionally, when forming powdery absorbent resin (for example, in a sheet form), etc., the absorbency under load and the absorbing rate of the resulting absorbent material are significantly reduced. However, in the present invention, a high value molding particle (absorbent material) can be obtained.

As described, according to the present invention, by pressurizing the water-containing gel or cellular gel, and reducing a water content in the water-containing gel or cellular gel, absorbent material (absorbent material (I) or absorbent material (II)) having excellent absorbing properties particularly in absorbing rate and absorbency under load can be obtained compared with conventional absorbent material.

Namely, when pressurizing the water-containing gel of the hydrophilic crosslinked polymer or cellular gel of the resulting hydrophilic polymer, by removing the aqueous solvent from the three-dimensional net structure of the water-containing gel or the cellular gel, the three-dimensional net structure is distorted under an applied pressure.

Therefore, for example, by pressurizing the gel composition 10 containing the water-containing gel as the gel, as shown in FIG. 2(a), the water content of the non-cellular absorbent resin 30 as a cross-linked gel-like hydrophilic polymer particles is reduced, and is greatly compressed in a direction of applying pressure, while being calendered in a direction of expanding in a perpendicular direction with respect to a pressurizing direction.

As shown in FIG. 3(a), by pressurizing the gel composition 10 containing cellular gel as the gel, cellular gel particles, i.e., the absorbent resin 31 having foams 31a inside as gel-like hydrophilic polymer particles are compressed in a large degree in a pressurizing direction for a reduction in amount of water content, while being calendered in a direction perpendicular to a pressurizing direction.

As a result, these absorbent resins 30 and 31 are compressed and immobilized in oblately distorted state to have a compression ratio of not less than 2, preferably in a range of from 5 to 1,000, more preferably in a range of from 10 to 200, and still more preferably in a range of from 15 to 100.

According to the present invention, the compression ratio suggests the expansion ratio in the direction of calendering the absorbent resin with respect to the compression ratio in the direction of compressing the absorbent resin.

Therefore, the compression ratio of respective absorbent resins 30 and 31 can be measured by the following method. Here, as the absorbent resin 30, the primary water containing gel may be used. Additionally, as the absorbent resin 31, the primary particle of the cellular gel may be used.

In the case of adopting the compression ratio of the absorbent resin 30, first, an average particle diameter of the absorbent resin 30 is obtained. Next, the thickness of the absorbent resin 30 after an applied pressure in the compressing direction and the average length (diameter) $D_2$ in a calendering direction are measured in a unit 0.01 mm, for example, by a slide caliper. Then, the compression ratio X is obtained by dividing the thickness $D_1$ in the compressing direction of the absorbent resin 30 under an applied pressure by an average particle diameter of the absorbent resin 30. Then, an expansion ratio Y is obtained by dividing the average length (diameter) $D_2$ in the driving direction of the absorbent resin after having an applied pressure by an average particle diameter of the resulting absorbent resin 30. In the described operation, the measurement is made with respect to from 10 to 100 particles, and a compression ratio of the absorbent resin 30 is obtained with an average value of Y/X.

The compression ratio of the absorbent resin 31 can be measured in the same manner as that adopted in measuring the compression ratio of the absorbent resin 30. Namely, first, the average particle diameter of the absorbent resin 31 is obtained. Next, the thickness $D_3$ in the compressing direction of the absorbent resin 31 after being pressurized, and the average length (diameter) $D_4$ in the calendering direction are measured in a unit of 0.01 mm, for example, by a slide caliper. Then, by dividing the thickness $D_3$ in the compressing direction of the absorbent resin 31 after having an applied pressure by the average particle diameter of the absorbent resin 31, a compression ratio X is obtained. Similarly, by dividing the average length (diameter) $D_4$ in the calendering direction of the absorbent resin 31 under an applied pressure with an average particle diameter of the resulting absorbent resin 30, the expansion ratio Y is obtained. In the described operation, the measurement is made with respect to from 10 to 100 particles, and based on the average value of Y/X, the compression ratio of the absorbent resin 31 is obtained.

When the compression ratio is less than 2, the compressed absorbent resins 30 and 31 become bulky, and this makes it difficult to reduce the size of the absorbent material and the size of the absorbent article containing the absorbent material. When the compression ratio is less than 2, the distortion of the absorbent resin can be minimized, and it is difficult to ensure a significant improvement in the absorbing rate. Additionally, in the case where the compression ratio exceeds 1,000, the absorbent resins 30 and 31 would be largely distorted, and the shapes are broken, and this makes it difficult to restore the original shape of the absorbent resin after being swollen by absorbing water.

As described, the absorbent resins 30 and 31 have the distorted cross-linked structure under an applied pressure (compression), and thus compressed, immobilized (unmovable) in an oblately distorted state. As a result, the absorbent resins 30 and 31 have distorted energy inside, and when contacting water, distorted energy is released, thereby generating an internal stress of a size different in respective coordinate axes (x, y, z) against the distortions of the cross-linked structure.

Therefore, when contacting water, the absorbent resin 30 quickly absorbs water to retain its original shape (shown in FIG. 2(b)), and is swollen by quickly absorbing water so as to have an anisotropy by the internal stress.

Namely, from the original state in the gel form shown in FIG. 2(b), the absorbent resin 30 is compressed to be restored in a stage before applying pressure shown in FIG. 2(b). Then, the absorbent resin 30 is swollen by absorbing water, thereby restoring the original shape before applying pressure. The absorbent resin 30 has the same shape before and after applying pressure.

When contacting water, the absorbent resin 31 absorbs water quickly, and in order to restore the state before applying pressure (compressing) shown in FIG. 3(b), the absorbent resin 31 is swollen (anisotropic swelling) so as to have an anisotropy by the inner stress.

Namely, the absorbent resin 31 is formed into the compressed state shown in FIG. 3(a) under an applied pressure from the initial state of the gel (shown in FIG. 3(b)), and as a result of swelling by absorbing water, it is retained in the original state shown in FIG. 3(b). There is no change in the shape of the absorbent resin 31 before and after having a pressure applied thereto.

Moreover, as shown in FIG. 3(a) and FIG. 3(b), as the absorbent resin 31 has foams 30a, a BET specific area (when drying) of not less than 30 times of the non-foamed absorbent resin 30 and has a sufficient liquid introducing space required for moving the aqueous liquid inside. Therefore, as described, according to the present invention, when the absorbing rate is not more than 20 seconds, and the absorbency under load is not less than 30 g/g, excellent absorbing properties can be obtained.

U.S. Pat. No. 4,920,202, U.S. Pat. No. 5,075,344, and U.S. Pat. No. 5,145,906 disclose a method of drying the water-containing gel of the hydrophilic crosslinked polymer, and further by pulverizing, if necessary, to obtain absorbent resin powders.

However, by simply drying the gel, the gel shrinks in an equivalent direction, the resulting absorbent resin is dried without being distorted and formed into powders. As a result, the resulting powdery absorbent resin is swollen by absorbing water in a similar shape.

In contrast, in the present invention, by reducing the water content while applying pressure, the distorted gel shrinks in the distorted state to retain its original shape. For the shape retaining property, it is the essential conditions that the absorbent resin (absorbent resins 30 and 31) has a cross-linked structure, and the state of the absorbent resin before an applied pressure is in a gel state, and it is impossible to restore the shape for the polymer which does not have the cross-linked structure.

As described, according to the absorbent material (I) containing the absorbent resin 30 and the absorbent material (II) of the present invention containing the absorbent resin 31 show excellent properties in their absorbing rate and the absorbency under load and the shape retaining property as the absorbent resins 30 and 31 retain their original shapes before having an applied pressure.

The water content of the water-containing absorbent materials (I) and (II) of the present invention is preferably in a range of from not more than 80 percent by weight, more preferably in a range of from 5 percent by weight to 50 percent by weight, and more preferably in a range of from 5 percent by weight to 30 percent by weight, and still more preferably in a range of from 6 percent by weight to 25 percent by weight. The respective water content of the absorbent materials (I) and (II) may be adjusted, for example, by reducing the water content of the gel under an applied pressure. However, the water content may be adjusted after having an applied pressure if necessary by adding water or drying.

The respective water content of the absorbent materials (I) and (II) indicate the ratio of the aqueous solvent based on the total amount of the aqueous solvent, the hydrophilic crosslinked polymer and the polyhydric alcohol contained in respective absorbent materials (I) and (II). In the case where the absorbent materials (I) and (II) contain the subsidiary forming material or other materials, when computing the water content, the subsidiary forming material or other forming materials are not considered.

The respective methods of measuring the water (content), the absorbency under load and absorbing rate are described in detail under preferred embodiments of the present invention. It should be noted here that the above-defined water content is the theoretical value; on the other hand, values of the water contents to be described in the below-discussed preferred embodiments are measured values. However, as no significant difference exists between them, it can be assumed that these measured values are the practical values for water content.

In the present invention, by calendaring the gel composition 10 using the drum dryer 1 attached to the compressor, the gel composition 10 can be processed successively. Namely, the absorbent material (I) or the absorbent material (II) can be manufactured successively.

The resulting sheet-like absorbent materials (I) and (II) have excellent flexibility, and, for example, have the degree of flexibility measured by the Gurley Stiffness Test of not more than 1,000 mgf, more preferably not more than 500 mgf, and more preferably not more than 200 mgf, and most preferably not more than 100 mgf. The method of measuring the flexibility will be explained under preferred embodiments of the present invention.

As described, the method (i) of manufacturing the absorbent material (I) of the present invention is a method of reducing the water content while pressurizing (calendaring) the water-containing gel of the hydrophilic crosslinked polymer. In the present invention, it is preferable that the water-containing gel further include a polyhydric alcohol. Furthermore, in the present invention, it is preferable that the water content in the water-containing gel is in a range of from 30 percent by weight to 90 percent by weight. Additionally, the absorbent material (I) is obtained in particles. However, it is preferable to calendar the water-containing gel to form it into a sheet.

For the manufacturing method (ii) of the absorbent material (II) of the present invention, a method of pressurizing the cellular gel of the hydrophiliccrosslinked polymer, preferably, a method of reducing the water content of the cellular gel under load is adopted. In the present invention, it is further preferable that the cellular gel contain the polyhydric alcohol. Furthermore, the water content in the cellular gel is preferably in a range of from 30 percent by weight to 90 percent by weight. According to the manufacturing method (ii), as in the manufacturing method (i), a particulate absorbent material (II) may be obtained; however, it is preferable to form the cellular gel by calendaring the cellular gel.

The manufacturing methods (i) and (ii) contain the absorbent resin which is swollen by absorbing water so as to have anisotropy, thereby providing absorbent materials (I) and (II) which have excellent properties particularly in absorbing properties such as absorbing rate and absorbency under load and shape retaining property.

Furthermore, as the water-containing gel and the cellular gel of the hydrophilic cross-linked polymer further include polyhydric alcohol, these gels are formed into a sheet with ease. Therefore, from these gels, the sheet-like absorbent material can be obtained directly from the gel, and the absorbent materials (I) and (II) having excellent flexibility and strength, cushioning characteristic, etc., can be obtained.

Furthermore, in the manufacturing method (i), with a combined use of the surface cross-linking agent, or by specifying the kind of the main chain of the hydrophilic cross-linked polymer, the water content and the water-soluble content in the water-containing gel of the hydrophilic crosslinked polymer, the average particle diameter, the dried average particle diameter, etc., of the shape retaining property of the resulting absorbent resin (absorbent resin 30) and the absorbent material (I) containing the absorbent resin can be still improved.

Additionally, in the manufacturing method (ii), with a combined use of the surface cross-linking agent, or by specifying the kind of the main chain of the hydrophilic crosslinked polymer, the water content and the water-soluble content of the cellular gel of the hydrophilic crosslinked polymer, the average particle diameter or the dried average particle diameter of the cellular gel, still improved shape retaining property of the absorbent resin (absorbent resin 31) and the absorbent material can be achieved.

Moreover, according to the manufacturing method (i) or (ii), the absorbent material (I) or (II) in which the hydrophilic crosslinked polymer is immobilized can be manufactured without once forming the gel of the hydrophilic polymer, i.e., the water-containing gel or the cellular gel, into powders. As various processes such as the process of drying, pulverizing, classifying, etc., can be eliminated, easy handling and improved working conditions can be achieved without generating dust. This permits a simplified manufacturing process and an improved yield. As a result, a sheet-like absorbent material can be manufactured at low cost directly from the water-containing gel or the cellular gel without using a fixing material such as a non-woven fabric. The described method also permits an absorbent material having a higher content of the hydrophilic cross-linked polymer, i.e., the absorbent resin to be achieved.

Furthermore, according to the manufacturing method (i) or (ii), the flexibility and the strength can be applied to the resulting absorbent material (I) or (II), and the gel can be calendared into a sheet, the absorbent material (I) or (II) is wound into a roll, etc., to apply an extension force. As a result, the absorbent material (I) and the absorbent material (II) can be manufactured successively.

When forming the absorbent materials (I) and (II) into a sheet, pressure and heat are applied to generate a temperature difference between the first face and the second face of the sheet.

According to the manufacturing method, by applying pressure and heat simultaneously to generate a temperature difference between the first face and the second face of the sheet, a difference occurs in the degree of distortion of the cross-linked structure of the absorbent resin between the first face and the second face of the sheet. Therefore, when swelling by absorbing water, the retaining of the absorbent resin differs between the first face and the second face of the sheet, the resulting absorbent material (I) or (II) is swollen while being curled so as to have a curvature. Therefore, when applying the resulting absorbent material (I) or (II) to the sanitary material such as paper diaper, sanitary napkin, etc., (absorbent articles) are fit along the body line and can be prevented from liquid leakage.

The absorbent resin compound (I) resulting from the manufacturing method contains the absorbent resin (absorbent resin 30) that is swollen by absorbing water so as to have anisotropy. Furthermore, the absorbent material (II) resulting from the manufacturing method contains the absorbent resin (absorbent resin 31) that is swollen by absorbing water so as to have anisotropy.

Namely, for example, the hydrophilic crosslinked polymer particles as the absorbent resin (absorbent resins 30 and 31) of the present invention are compressed by separating the aqueous solvent from the three-dimensional net structure of the gel particles when applying the gel particles of the hydrophilic crosslinked polymer. Therefore, the distortion by compression occurs in the three-dimensional net structure of the absorbent resin (absorbent resins 30 and 31). Therefore, the absorbent resin (absorbent resins 30 and 31) has a distorted energy inside, and in order to restore the state before being compressed, the absorbent resin is swollen so as to have anisotropy by quickly absorbing water in contact water.

As a result, the absorbent resins (absorbent resins 30 and 31) are restored in the stage before being decompressed without distortion. Namely, the absorbent resin (absorbent resin 30 or 31) retains the original state before being compressed. In the present invention, the compressed ratio indicates the degree of compression of the absorbent resin (absorbent resins 30 and 31). In order to obtain sufficient effects of improving absorbency, the compression ratio is in a range of from 2 to 1,000. As described, the absorbent resin (absorbent resins 30 and 31) of the present invention offers various absorbing properties such as excellent absorbing rate and absorbency under applied load, etc., and shape retention as force is exerted to restore the state before compression with respect to the distorted cross-linked structure, the absorbency under load, and the shape retaining property.

Additionally, it is preferable that the absorbent resin in accordance with the present invention has foams inside. As the absorbent resin has foams inside, a sufficient space for passing liquid is ensured to allow the aqueous liquid to move inside the absorbent resin. Therefore, in the case where foams are included inside the absorbent resin, excellent permeability to aqueous liquid and diffusion, absorbing rate and the water retention by capillarity can be achieved.

As described, the absorbent resin (absorbent resins 30, 31) of the present invention show excellent various absorbing properties such as absorbing rate and the absorbency under load, etc., and shape retaining property. The absorbent materials (I) and (II) of the present invention including the absorbent resin (absorbent resins 30 and 31) also have various absorbing properties such as the absorbing rate and the absorbency under load, etc., and the shape retaining property.

The shape of the absorbent materials (I) and (II) of the present invention self-retains, and thus the amount of the hydrophilic cross-linked polymer, i.e., the absorbent resin per unit area can be increased as compared to the conventional absorbent material where the absorbent resin is sandwiched between the absorbent materials such as pulp, non-woven fabric, etc. Therefore, the absorbency and absorbing rate under load can be improved from the conventional arrangement. Namely, the absorbent materials (I) and (II) absorb the aqueous liquid quickly when contacting aqueous liquid such as water, body fluid, drip, etc. The absorbent materials (I) and (II) have the respective water contents of not more than 80 percent by weight, and if necessary contain the polyhydric alcohol and the subsidiary forming material. Additionally, sheet-like absorbent materials (I) and (II) are obtained by the described method. They have the absorbing rate of not more than 150 seconds, and the absorbency under load of not less than 15 g/g, preferably not less than 20 g/g, more preferably not less than 25 g/g and still more preferably not less than 30 g/g.

When the absorbent materials (I) and (II) contain the polyvalent alcohol, the absorbent materials (I) and (II) show excellent flexibility, strength and cushioning. Additionally, when the absorbent materials (I) and (II) have still desirable shape retaining property, improved flexibility and strength can be achieved.

Furthermore, as the absorbent materials (I) and (II) have the absorbent resin (absorbent resins 30 and 31) which is swollen so as to have anisotropy to retain the original state before being compressed, by molding such that a difference in distortion between the cross-linked structure of the absorbent resin of the heated portion (heating face) and the cross-linked structure of the absorbent resin of the non-heated portion (heating face) by partially heating the absorbent material (I) or (II), the resulting absorbent material (I) or (II) is swollen while being curled so as to have a curvature even in a flat sheet form.

When adopting the absorbent material for, for example, sanitary material (absorbent article) paper diaper, sanitary napkin, etc., by curling the absorbent material along the curve of the absorbent material, it can be fitted to the body line so as to form a curve to prevent liquid from leaking.

Additionally, it is preferable that the absorbent materials (I) and (II) are formed into a sheet so as to have a flexibility of not more than 1,000 mgf. As a result, the absorbent materials (I) and (II), and softness and desirable use can be applied to the absorbent article having the absorbent materials (I) and (II).

The above explanations will be given through the case where the absorbent materials (I) and (II) are formed into a sheet. However, it is permitted to form them to have a block shape, a plate shape and a film shape, etc., and they can be formed into powders by pulverizing, but the forms are not particularly limited.

Additionally, the sheet-like absorbent materials (I) and (II) (sheet) of the present invention have a thickness in a range of from 0.01 mm to 5 mm, preferably from 0.1 mm to 3 mm, and still more preferably in a range of from 0.5 mm to 1 mm. By adjusting the compression ratio, the film thickness can be adjusted with ease. For example, by adjusting the time, the temperature, the clearance between the compressor and the drum dryer, the compression ratio can be adjusted with ease.

Furthermore, the absorbent materials (I) and (II) may be formed into a sheet by once forming it in a powdery form after applying a pressure to the water-containing gel of the hydrophilic cross-linked polymer or the cellular gel of the hydrophilic cross-linked polymer. In view of the convenience in handling, working environment, productivity, etc., it is preferable that the water-containing gel and the cellular gel contain polyhydric alcohol, and that these gels are formed directly into sheets without once forming them into powders.

Although explanations have been given through the case where the absorbent material (I) and the absorbent material (II) having such a structure that a mixture of the water-containing gel or the cellular gel and polyhydric alcohol are mixed with a fiber as a subsidiary forming material, the structure of the absorbent material (I) and the absorbent material (II) is not particularly limited.

Other than the described mixed structure of the mixture and the fiber, the absorbent material (I) and the absorbent material (II) may have the structure wherein the mixture is held by a plurality of fibers formed into a sheet such as non-woven fabrics, woven fabrics; paper, etc.; the arrangement wherein after mixing the mixture and the fibers to be formed into sheets, the resulting fibers formed into a sheet are held by a plurality of the sheets; a structure wherein after mixing the mixture and the fibers to be formed into sheets, the sheet is sandwiched by a plurality of fibers formed into a sheet, etc.

The absorbent article of the present invention contains at least one absorbent material selected from the group consisting of the absorbent material (I) and the absorbent material (II) having the described structure. Namely, the absorbent materials (I) and (II) themselves can be formed into the absorbent article, or the absorbent material (I) and the absorbent material (II) can be combined with other material. The structure of the absorbent article is not particularly limited. In the case of applying the absorbent article, for example, to paper diapers (disposal diapers), sanitary napkins, incontinence pads, it is preferable to adopt a) a structure wherein the sheet like absorbent material (I) or the absorbent material (II) having the described arrangement is sandwiched by a liquid permeable sheet and a liquid impermeable sheet or b) a structure wherein the sheet like absorbent material (I) or the absorbent material (II) having the described arrangement is sandwiched between two liquid permeable sheets. The absorbent material (I) and the absorbent material (II) as the absorbent layer have excellent absorbing properties. Therefore, when adopting the absorbent article to paper diapers, the leakage of urine from the paper diapers can be prevented, and the user of the paper diaper can feel dry.

The sheet which is permeable to liquid (hereinafter referred to as liquid permeable sheet) is made of a material that is permeable to aqueous liquid. Examples of such liquid permeable sheet include but are not limited to: webs or mats, for example, regenerated cellulose fibers, non-woven fabrics, etc., woven fabrics made of a synthetic fiber such as rayon, etc., cotton card web, and the like; cotton pulp, paper; porous synthetic resin films made of polyethylene, polypropylene, polyesters, polyamide, and the like. The liquid permeable sheet may be formed into a bag having a size sufficient for storing the absorbent material.

The sheet that is not permeable to liquid (hereinafter referred to as liquid impermeable sheet) is made of a material which is not permeable to liquid. Examples of a material of such liquid impermeable sheet may be but are not limited to: synthetic resin film such as polyamide, polyethylene, polypropylene, polystyrene, poly vinyl chloride, etc.; a film made of a composite material of the synthetic resin and non-woven fabrics; a film made of a composite material of the synthetic resin and the woven fabrics, and the like. The liquid impermeable sheet is permeable to steam.

The method of manufacturing the absorbent article of the present invention is not particularly limited. The absorbent article is manufactured, for example, by laminating at least one absorbent material selected from the group consisting of the absorbent material (I) and the absorbent material (II), and the liquid impermeable sheet. Additionally, the sheets thus laminated may be subjected to a further process such as bonding the circumferential portion of the sheets to be immobilized, or partially bonding the sheets to be immobilized, or forming a slit or, a process such as an embossing process, etc. The absorbent product may be formed by laminating the liquid permeable sheet or the liquid impermeable sheet onto one surface of the sheet like absorbent material (absorbent material (I) or the absorbent material (II)). Furthermore, the absorbent material, i.e., the absorbent article may be formed by first placing (applying) the gel or the gel composition onto the liquid permeable sheet or the liquid impermeable sheet, and then applying pressure (calendaring). Furthermore, the absorbent article may be formed by first cutting the sheet like the absorbent material (I) and the absorbent material (II) into a strip, and then mixing it with cellulose fibers, etc.

In reference to FIG. 4, paper diapers as one application of the absorbent article of the present invention will be explained. Here, the application of the absorbent article of the present invention is not limited to the paper diapers.

As shown in FIG. 4, the paper diapers of the present invention are composed of a back sheet 21 (liquid impermeable sheet), an absorbent material 22 (the sheet-like absorbent material (I) or the sheet-like absorbent material (II)) and a top sheet 23 as a liquid permeable sheet, etc. The back sheet 21 and the top sheet 23 are formed into a predetermined shape. Then, the back sheet 21, the absorbent material 22 and the top sheet 23 are laminated in this order by a both-sided tape, etc. Then, a leg gather 24 and a waist gather 25 are formed at a predetermined position of the sheets thus laminated, and tape fasteners 26 are mounted at a predetermined position of the sheets, thereby preparing paper diapers as one application of the absorbent article.

The resulting paper diapers prepared from the absorbent material 22 show excellent absorbing properties such as absorbing rate, absorbency under applied pressure, and shape retaining property, and also show excellent flexibility and strength. Thus, the paper diapers permit the urine to be quickly absorbed, thereby providing desirable paper diapers which show a desirable use without leakage of urine, etc.

Moreover, as the absorbent resin 22 is swollen while being curled by absorbing water, the paper diaper can be fitted along the body line and offers an improved effect of preventing a leakage of liquid.

As described, as the absorbent product includes the absorbent material (at least one absorbent material selected from the group selected from the group consisting of the absorbent material (I) and the absorbent material (II)), the absorbent product which is excellent in various absorbing properties such as absorbing rate, absorbency under load, etc., and is soft and comfortable to use can be provided. As a result, the absorbent article which is comfortable to the skin of the user can be achieved.

Conventionally, the ratio of the hydrophilic cross-linked polymer based on the total weight of the absorbent product is relatively low, i.e., less than 40 percent by weight. In contrast, the described arrangement of the present invention has a high ratio of the hydrophilic cross-linked polymer based on the total weight of the absorbent product, i.e., generally in a range of from around 40 percent by weight to around 80 percent by weight, preferably from around 50 percent by weight to around 80 percent by weight, and still more preferably in a range of from around 60 percent by weight to around 80 percent by weight.

Accordingly, the present invention offers a thinner and compact size absorbent product while maintaining the absorbing properties in the same level as those of the conventional absorbent articles. Furthermore, as the absorbent materials (I) and (II) are formed by applying pressure to the water-containing gel and cellular gel, in processes including manufacturing, wrapping and transporting processes of the absorbent material (I) or the absorbent material (II) or the absorbent product, the hydrophilic cross-linked polymer does not move in the absorbent materials (I) and (II), and the absorbent materials (I) and (II) can be prevented from being dropped off. Furthermore, for example, when forming the absorbent materials (I) and (II) into sheets, different from the conventional absorbent material prepared by once forming the absorbent resin into a powdery form and then forming the resulting powdery absorbent resin into a sheet, the absorbent materials (I) and (II) of the present invention are kept in a sheet form even after being swollen by absorbing water. Thus, even after being swollen by absorbing water, the gel can be prevented from being dropped from the absorbent material (I) or the absorbent material (II).

The absorbent material (I) or the absorbent material (II) may optionally include a deodorant, perfume, various chemical agents, various inorganic agents, water-soluble polymers, plant growth accelerators, anti-bacterial agents, mildewproofing agents, foaming agents, pigments, dyes, carbon blacks, activated carbons, hydrophilic short fibers, fertilizers, oxidizing agents, reducing agents, water, salts, etc. to provide additional functions to the absorbent material (I) or (II) or to the absorbent article.

The absorbent material (I), the absorbent material (II) and the absorbent article of the present invention are suitable for use in sanitary materials such as paper diapers (disposable diapers), sanitary napkins, and tampons, so-called incontinence pads, etc., moisture condensation absorbent sheets, agricultural water retaining materials, waterproofing agents for civil engineering works, medical materials, such as medical sheets, bed pads, etc., materials for keeping foodstuffs fresh, and materials for preventing foodstuffs from dripping, towels, bandages, etc., for the purpose of absorbing aqueous solution and moisture. The applications of the absorbent material (I) and the absorbent material (II) and the absorbent material are not limited to the above examples.

BRIEF EXPLANATIONS OF THE DRAWINGS

FIG. 1 which shows one example of the manufacturing method of an absorbent material of the present invention is a cross-sectional view schematically showing a drum dryer provided with a calendaring device;

FIG. 2($a$) is an explanatory view showing a compressed state of the non-cellular absorbent resin contained in the absorbent material of the present invention;

FIG. 2($b$) is an explanatory view showing the state where the absorbent resin of FIG. 2($a$) is swollen by absorbing water;

FIG. 3($b$) is an explanatory view showing a state where the absorbent resin shown in FIG. 3($a$) is swollen by absorbing water.

PREFERRED EMBODIMENTS OF THE PRESENT INVENTION

Figure 1:
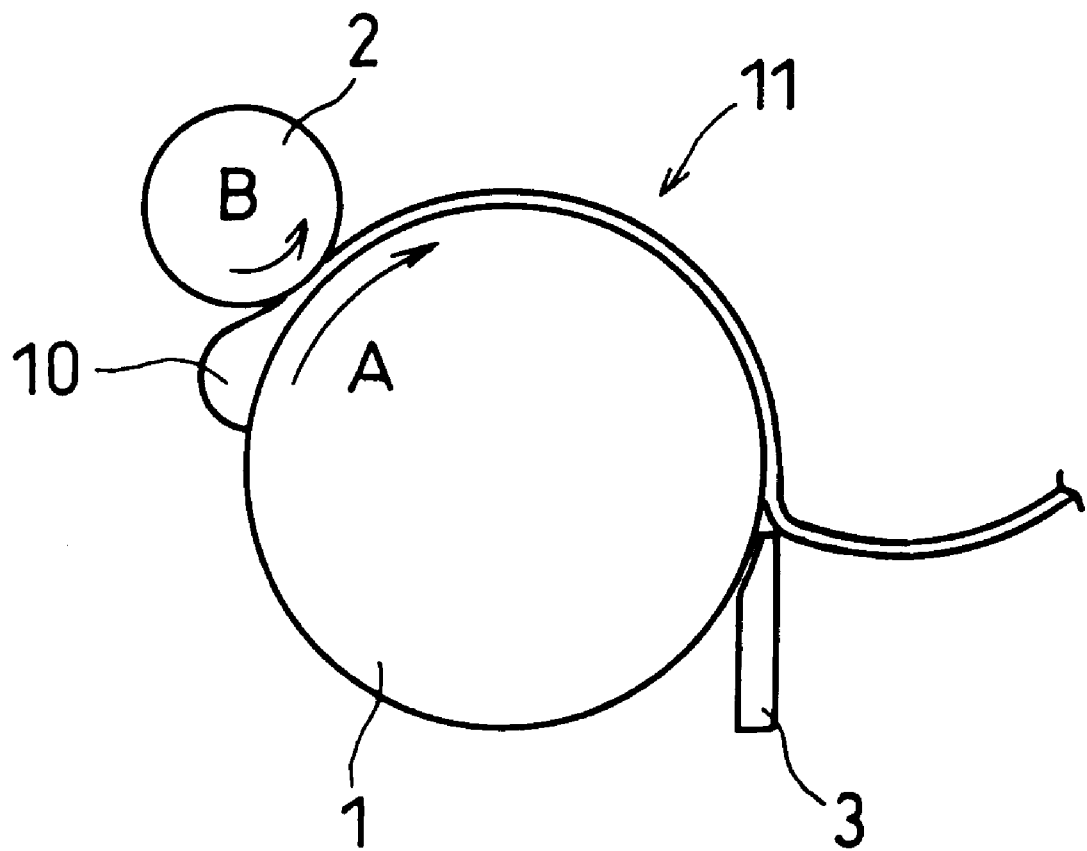
Figure 3A:
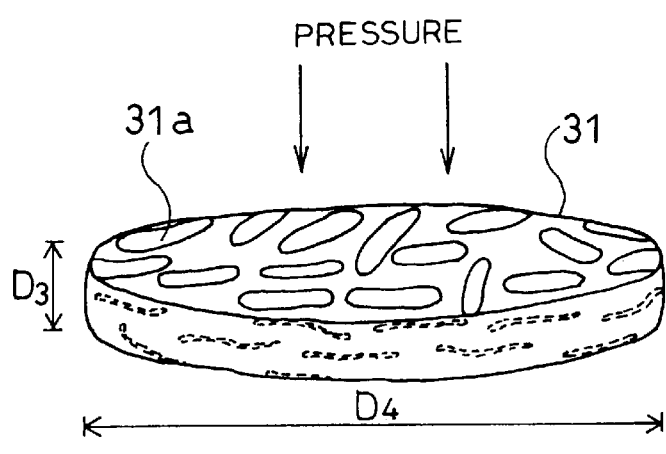
FIG. 3($a$) is an explanatory view showing a compressed absorbent resin having foams inside in another absorbent material of the present invention.
Figure 3B:
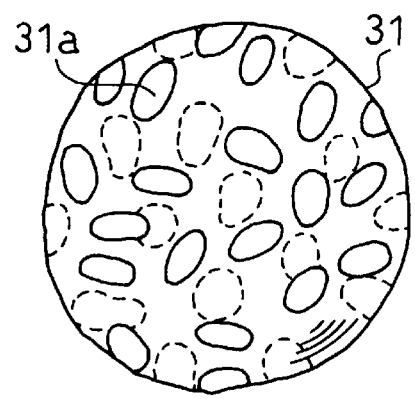
Figure 4:
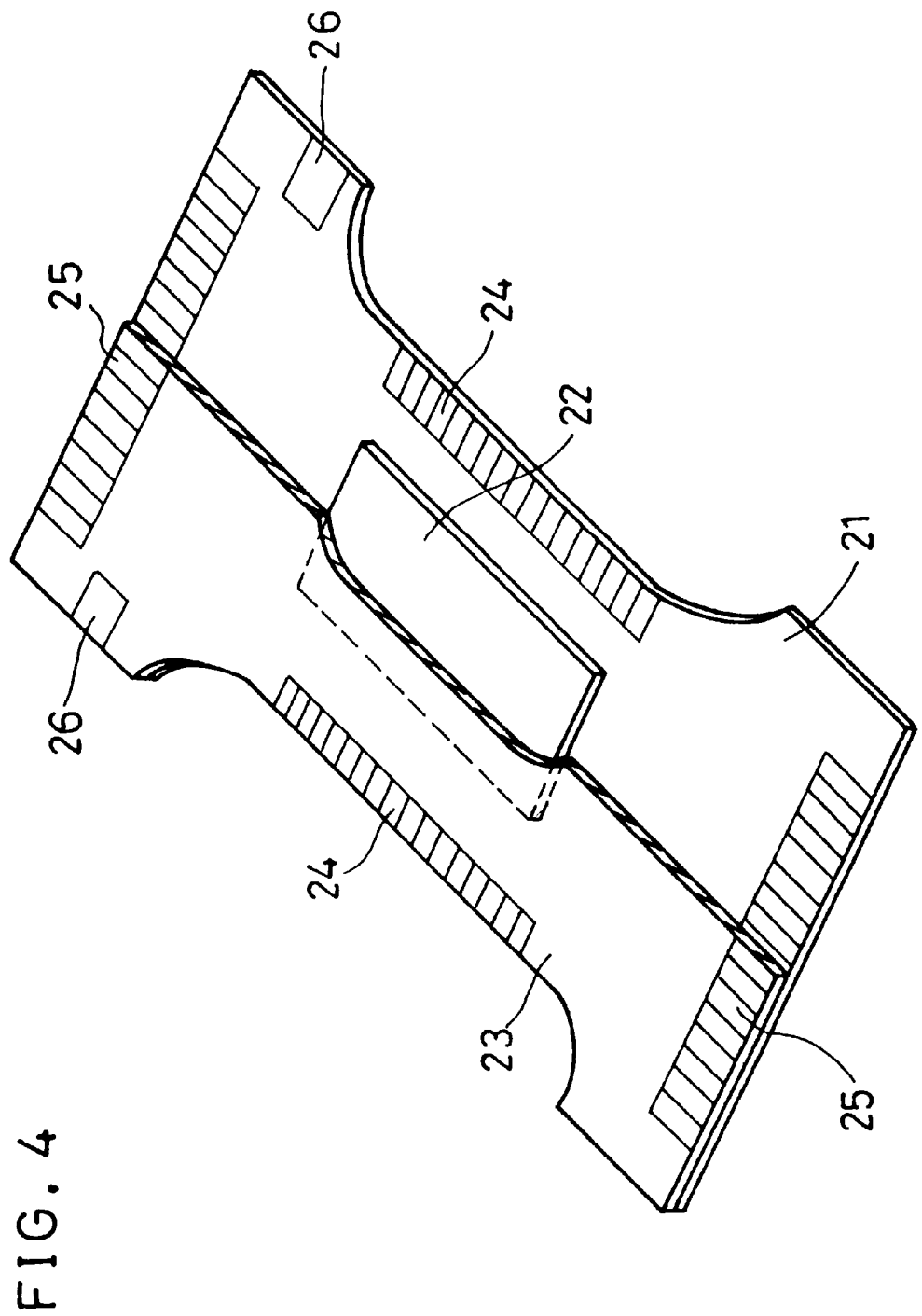
FIG. 4 is a perspective view schematically showing a partial cut off surface of a paper diaper as an example of the absorbent article adopting the absorbent material of the present invention.

The present invention will be described in detail by way of examples and comparative examples. However, the present invention is not limited to the disclosure below. The performances of absorbent materials were measured in the following manner.

(a) Water Content

First, a sheet-like absorbent material was cut into a size of 10 cm square, and the weight $W_0$ (g) of the absorbent material (hereinafter referred to as a cut sheet) was measured. The cut sheet was placed in an oven maintained at 180° C. (Tokyo Rika Kiki Co., Ltd.: type NDO-450) and was left for 3 hours. Then, the cut sheet was taken out, and was placed in a desiccator in which silicagel was placed, and the cut sheet was cooled off for 5 minutes. Then, the weight $W_1$ (g) of the sheet was measured. By substituting the weight $W_0$ (g) and the weight $W_1$ (g) into the following formula, the water content (percent by weight) was determined.

Water content (wt %)
= [(weight $W_0$ (g) − weight $W_1$ (g))/ Weight $W_0$ (g)] × 100.

(b) Absorbency

Here, 0.2 g of the absorbent material was uniformly placed into a tea bag (60 mm×60 mm) made of non-woven fabric, and the opening of the tea bag was heat sealed. Then, the tea bag was immersed into a 0.9 percent by weight sodium chloride solution (physiological saline solution) for 30 minutes. Then, the tea bag was taken out, and was subjected to hydro-extraction for 3 minutes at 250 G using a centrifugal separator, and the weight $W_2$ (g) of the tea bag was measured. Further, the same processes were carried out with an empty bag, and the weight $W_3$ (g) of the empty tea bag was measured. The absorbency (g/g) of the sampled absorbent material was determined by substituting the weight $W_2$ and the weight $W_3$ into the following formula:

Absorbency (g/g)
=(Weight $W_2$ (g) − Weight $W_3$ (g))/ Weight (g) of the Absorbent Material.

(c) Absorbency Under Load

First, in a glass petri dish having an inner diameter of 160 mm and a height of 20 mm, a glass filter plate (G#1) having a diameter of 120 mm was placed. Then, a 0.4 percent by weight aqueous saline solution was poured into the petri dish. The aqueous saline solution was added in an amount such that the surface of the aqueous saline solution was in substantially the same level as the filter plate. Next, a filter paper (TOYO FILTER PAPER No. 2 available from Toyo Filter Co., Ltd.) was placed on the filter plate.

Then, for the sheet-like absorbent material in a sheet form, it was cut into a size of 3.1 cm square, and the weight $W_4$ (g) of the absorbent material (hereinafter referred to as a cut sheet) was measured. Then, a metal gauze made of stainless steel having a 400-mesh was fixed on the bottom portion of an acrylic resin cylinder having an inner diameter of 55 mm and a height of 60 mm, thereby preparing a support cylinder. The cut sheet was placed in the support cylinder, i.e., on the metal gauze, and a cylindrical brass plunger was placed as a weight, thereby preparing a measuring cylinder. The weight of the plunger was adjusted so as to be capable of uniformly applying a load of 50 g/cm². Then, the total weight of the cut sheet, the support cylinder and the plunger, i.e., the weight $W_5$ (g) of the measuring cylinder was measured.

Then, the measuring cylinder was placed on the filter paper. The saline solution was absorbed by the cut sheet in the measuring cylinder for 30 minutes after the measuring cylinder was placed on the filter paper. Namely, a 0.4 percent by weight saline solution was absorbed by the cut sheet under load. While the saline solution was being absorbed by the cut sheet, a 0.4 percent by weight saline solution was added to the petri dish until the surface of the saline solution became substantially the same level as the upper surface of the filter plate. After an elapse of time of 30 minutes, the weight $W_6$ of the cylinder was measured. Then, by substituting the resulting weights $W_4$, $W_5$ and $W_6$ into the following formula, the absorbency under load (g/g) was determined.

Absorbency under Load (g/g)=(Weight $W_6$(g)−Weight $W_5$(g))/ Weight $W_4$(g)).

On the other hand, for the powdery absorbent material, in place of the sheet of a size of 3.1 cm square, 0.9 g of the absorbent material was uniformly dispersed in the acrylic resin cylinder, and the absorbency under load of 50 g/cm$^2$ was measured. Then, the absorbency under load (g/g) was determined according to the above formula.

(d) Absorbing Rate

For a sheet-like absorbent material, first, it was cut into a size of 2.54 cm square (1 inch$^2$), and the weight of the absorbent material (hereinafter referred to as a cut sheet) was measured. On the other hand, into a polypropylene container having an inner diameter of 55 mm and a height of 15 mm, a physiological saline solution was poured into a weight of 10 times based on the weight of the cut sheet, and the cut sheet was placed in the physiologic saline solution. Then, the time required for the saline solution to be completely absorbed by the cut sheet after the cut sheet was placed in the physiologic saline solution was measured, and the resulting time was determined to be the absorbing rate (seconds). In this measurement, it was checked to see if the physiological saline solution had been completely absorbed by the cut sheet by the existence of the remaining liquid of the physiological saline solution by tilting the polypropylene container at 45°. Namely, the point from which the remaining liquid no longer existed was determined to be the point where all the physiological saline solution was absorbed by the cut sheet.

In the case of the powdery absorbent material, in place of the sheet of a size of 2.54 cm square, the absorbing rate was measured using 1 g of the absorbent material in the same manner.

(e) Flexibility

The flexibility was measured with respect to only the sheet-like absorbent material according to the Gurley Stiffness Test defined in JIS L 1096. The flexibility was determined such that the smaller value (flexibility) measured by the method indicated the higher flexibility.

EXAMPLE 1

A jacketed stainless steel kneader having an inner volume of 10 liters and provided with two sigma shaped vanes having a rotation diameter of 120 mm was prepared as a reactor. The kneader has a lid for sealing the inside of the system, and a lid for applying a pressure of 66 kg to contents placed therein. In the reactor, 5,000 g of 38 percent by weight aqueous solution of acrylic acid (monomer component) and sodium acrylate (monomer component) (75 mole percent of the total monomer components in the aqueous solution is neutralized) and 2.85 g of trimethylolpropane triacrylate as a cross-linking agent (hereinafter referred to as a cross-linking agent (A)) were placed and nitrogen gas was blown in to displace the air entrapped in the reaction system. The amount of use of the cross-linking agent (A) with respect to the monomer component was 0.045 mole percent.

The kneader was heated by passing hot water at 30° C. through the jacket, while stirring the contents of the kneader, and sodium persulfate and L-ascorbic acid were added as polymerization initiators to the contents of the kneader. As a result, the polymerization started after an elapse of time of around 1 minute. Based on the monomer component, the respective amounts of use of the sodium persulfate and L-ascorbic acid were 0.12 mole percent and 0.005 mole percent respectively.

Then, after carrying out a polymerization at 30° C. for 60 minutes, the pressurizing lid was placed on the resulting bulk-like water-containing gel (contents), and the gel was stirred for 20 minutes and was divided into fine pieces. As a result, finely divided water-containing gel having a particle diameter in a range of from 0.2 mm to 0.8 mm was obtained. The solid portion of the water-containing gel was 38 percent by weight.

Then, 800 g of finely divided water-containing gel was placed in another kneader having the same arrangement as the described kneader. Then, a mixed solution of 33.8 g of glycerol as a polyvalent alcohol and 0.31 g of ethylene glycol diglycidyl ether as surface cross-linking agent (Denacol EX-810 available from Nagase Chemical Industry Co., Ltd., hereinafter referred as a surface cross-linking agent (B)) was prepared.

The kneader was heated by passing hot water at 70° C. through the jacket, while stirring the contents of the kneader. Then, with stirring, the mixed solution was added to the water-containing gel, and was stirred until both are uniformly mixed. Based on 100 parts by weight of the solid portion of the water-containing gel, the amounts of use of glycerol and the surface cross-linking agent (B) were 11.1 parts by weight and 0.1 parts by weight respectively.

Next, to the resulting mixture, 10.4 g of polyester fibers (auxiliary molding compound) having a length of from 2 mm to 3 mm made of polyethylene terephtalate was added to the resulting mixture little by little and was kneaded until the agglomeration of the fibers disappeared. The amount of the polyester fiber with respect to 100 parts by weight of the solid portion of the water-containing gel was 3.4 parts by weight, thereby obtaining a water-containing gel composition.

Thereafter, the water-containing gel composition was calendared by an open-type single drum dryer (available from Katsuragi Co., Ltd., TYPE: NRXM 750-N35C) and the compressor provided therewith, and a contact surface between the water-containing gel composition (1) and the drum dryer was heated to 150° C. Thereafter, the resulting sheet was scraped off by the scraper from the surface of the drum dryer. As a result, a sheet-like absorbent material having a thickness of 0.8 mm was obtained. The main conditions for manufacturing the water-containing gel are summarized in Table 1.

The resulting absorbent material had a weighing of 490 g/m$^2$, a water content of 7.5 percent by weight, an absorbency of 30.2 g/g, an absorbency under load of 25.2 g/g, and an absorbing rate of 68 seconds. These results of measurements were summarized in Table 2.

COMPARATIVE EXAMPLE 1

The water-containing gel composition resulting from Example 1 was heated to 150° C. by means of only the drum dryer without using the compressor, and was formed into a sheet without calendaring. Thereafter, the resulting sheet was scraped off by the scraper from the surface of the dryer drum. As a result, a sheet-like absorbent material was obtained. The results of measurements of the resulting absorbent material were summarized in Table 2.

COMPARATIVE EXAMPLE 2

The water-containing gel composition resulting from Example 1 was calendared without heating the dryer drum. As a result, the water-containing gel composition was formed into a sheet without reducing the water content of the water-containing gel. Thereafter, the resulting sheet was scraped off using the scraper from the surface of the drum dryer (temperature of 25° C.). As a result, a sheet-like absorbent material was obtained. The results of measurements of the resulting absorbent material are summarized in Table 2.

COMPARATIVE EXAMPLE 3

The sheet-like absorbent material resulting from comparative example 2 was dried in a hot air circulating type dryer maintained at 105° C. Namely, after the water-containing gel was calendared, the water content was reduced. The results of measurements of the absorbent material are summarized in Table 2. The resulting absorbent material showed poor shape retaining property, and the flexibility of the sample could not be measured.

EXAMPLE 2

Except that 76 g of glycerol was used in place of the mixed solution of Example 1, the reaction and operations of example 1 were repeated, thereby obtaining a sheet-like absorbent material. In this example, 25 parts by weight of glycerol were used based on 100 parts by weight of the solid portion of the water-containing gel. The main conditions for manufacturing the water-containing gel composition are summarized in Table 1. Additionally, the results of measurements of the resulting absorbent material are summarized in Table 2.

EXAMPLE 3

Except that a mixture of 76 g of glycerol and 0.31 g of the surface cross-linking agent (B) was used in place of the mixed solution of Example 1, the reaction and operations of Example 1 were repeated, thereby obtaining a sheet-like absorbent material. The main conditions of manufacturing the water-containing gel composition are summarized in Table 1. Additionally, the results of measurements of the resulting absorbent material are summarized in Table 2.

EXAMPLE 4

Except that a mixture of 76 g of glycerol and 1.53 g of the surface cross-linking agent (B) was used in place of the mixed solution of Example 1, the reaction and operations of Example 1 were repeated, thereby obtaining a sheet-like absorbent material. In this example, 0.5 parts by weight of the surface cross-linking agent (B) were used based on 100 parts by weight of the solid portion of the water-containing gel. The main conditions of manufacturing the water-containing gel composition are summarized in Table 1. Additionally, the results of measurements of the resulting absorbent material are summarized in Table 2.

EXAMPLE 5

Except that a mixture of 76 g of glycerol and 1.53 g of the surface cross-linking agent (B) was used in place of the mixed solution of Example 1, and that the amount of use of the polyester fiber was altered from 10.4 g to 16.0 g, the reaction and operations of Example 1 were repeated, thereby obtaining a sheet-like absorbent material. In this example, 5.3 parts by weight of the surface polyester fibers were used based on 100 parts by weight of the solid portion of the water-containing gel. The main manufacturing conditions of the water-containing gel composition are summarized in Table 1. Additionally, the results of measurements of the resulting absorbent material are summarized in Table 2.

EXAMPLE 6

Except that 304 g of glycerol were used in place of the mixed solution of Example 1, the reaction and operations of Example 1 were repeated, thereby obtaining a sheet-like absorbent material. Based on 100 parts by weight of the solid portion of the water-containing gel, the amount of use of glycerol was 100 parts by weight. The main conditions of manufacturing the water-containing gel composition are summarized in Table 1. Additionally, the results of measurements of the resulting absorbent material are summarized in Table 2.

EXAMPLE 7

Except that an amount of use of the cross-linking agent (A) of Example 1 was altered from 2.85 g to 1.27 g, and a mixed solution of 76 g of glycerol and 1.53 g of the surface cross-linking agent (B) was used in place of the mixed solution of Example 1, the reaction and the operations of Example 1 were repeated, thereby obtaining a sheet-like absorbent material. In this example, 0.02 mole percent of the cross-linking agent (A) were used with respect to the monomer component. The main conditions of manufacturing the water-containing gel composition are summarized in Table 1. Additionally, the results of measurements of the resulting absorbent material are summarized in Table 2.

EXAMPLE 8

Except that 5,000 g of 30 percent by weight aqueous solution of acrylic acid (monomer component) and sodium acrylate (monomer component) (75 mole percent of the total monomer components in the aqueous solution is neutralized) were used in place of an aqueous 38 percent by weight of sodium acrylate, and 7.18 g of polyethylene glycol diacrylate (ethylene glycol had an average additional number of moles of 8; hereinafter referred to as a cross-linking agent (C)) as a cross-linking agent, the reaction and operations of Example 7 were repeated, thereby obtaining a sheet-like absorbent material. In this example, 0.07 mole percent of the cross-linking agent (C) was used based on the monomer component. Additionally, the solid portion of the water-containing gel was 30 percent by weight. The main conditions of manufacturing the water-containing gel composition are summarized in Table 1. Additionally, the results of measurements of the resulting absorbent material are summarized in Table 2.

EXAMPLE 9

Except that a mixture of 76 g of glycerol and 0.31 g of the surface cross-linking agent (B) was used in place of the mixed solution of Example 1, and that the polyester fibers were not used (not added), the reaction and the operations of Example 1 were repeated, thereby obtaining a sheet-like absorbent material. The main conditions of manufacturing the water-containing gel composition are summarized in Table 1. Additionally, the results of measurements of the resulting absorbent material are summarized in Table 2.

EXAMPLE 10

Except that a mixture of 76 g of glycerol and 1.53 g of the surface cross-linking agent (B) was used in place of the mixed solution resulting from Example 1, and that 76 g of pulp fibers (auxiliary molding compound) having a fiber length of from around 10 mm to 20 mm was used in place of the polyester fibers, the reaction and operations of Example 1 were repeated, thereby obtaining a sheet-like absorbent material. In this example, 25 parts by weight of the pulp fibers were used based on 100 parts by weight of the solid portion of the water-containing gel. The main conditions of manufacturing the water-containing gel composition are summarized in Table 1. Additionally, the results of measurements of the resulting absorbent material are summarized in Table 2.

EXAMPLE 11

Except that polyester fibers having a fiber length of from around 20 mm to 30 mm were used, the reaction and the operations of Example 1 were repeated, thereby obtaining a sheet-like absorbent material. The absorbent material resulting from this example was superior to the absorbent material resulting from Example 1 in its shape retaining property in both dried and swollen states and the absorbing rate. The main conditions of manufacturing the water-containing gel composition are summarized in Table 1. Additionally, the results of measurements of the resulting absorbent material are summarized in Table 2.

TABLE 1

|   | A  | B     | C    | D   | Polyester Fibers E | Polyester Fibers F |
|---|----|-------|------|-----|------|-------|
| 1 | 38 | 0.045 | 11.1 | 0.1 | 3.4  | 2–3   |
| 2 | 38 | 0.045 | 25   | 0   | 3.4  | 2–3   |
| 3 | 38 | 0.045 | 25   | 0.5 | 3.4  | 2–3   |
| 4 | 38 | 0.045 | 25   | 0.5 | 3.4  | 2–3   |
| 5 | 38 | 0.045 | 25   | 0.5 | 5.3  | 2–3   |
| 6 | 38 | 0.045 | 100  | 0   | 3.4  | 2–3   |
| 7 | 38 | 0.02  | 25   | 0.5 | 3.4  | 2–3   |
| 8 | 30 | Cross-Linking Agent (C) 0.07 | 25 | 0.5 | 3.4 | 2–3 |
| 9 | 38 | 0.045 | 25   | 0.1 | 0    | 2–3   |
| 10| 38 | 0.045 | 25   | 0.5 | Pulp Fiber 25 | 10–20 |
| 11| 38 | 0.045 | 11.1 | 0.1 | 3.4  | 20–30 |

A: Solid Portion (% by weight)
B: Cross-Linking Agent (A) (mole %)
C: Glycerol (Parts by Weight)
D: Surface Cross-Linking Agent (B) (parts by weight)
E: (parts by weight)
F: (mm)

TABLE 2

|            | A    | B    | C    | D    | E   | F    |
|------------|------|------|------|------|-----|------|
| EXAMPLE 1  | 490  | 7.5  | 30.2 | 25.2 | 68  | 750  |
| COMP. EXAMPLE 1 | 510 | 8.2 | 29.8 | 24.4 | 92 | 930 |
| COMP. EXAMPLE 2 | 990 | 54.1 | 15.5 | 9.8 | 270 | —   |
| COMP. EXAMPLE 3 | 520 | 9.9 | 28.8 | 23.4 | 97 | 1020 |
| EXAMPLE 2  | 753  | 11.2 | 32.1 | 15.3 | 114 | 520  |
| EXAMPLE 3  | 474  | 16.2 | 24.2 | 25.1 | 71  | 260  |
| EXAMPLE 4  | 509  | 17.4 | 20.5 | 27.5 | 47  | 160  |
| EXAMPLE 5  | 273  | 12.9 | 22.2 | 27.5 | 23  | 490  |
| EXAMPLE 6  | 1108 | 17.8 | 21.6 | 17.8 | 83  | 310  |
| EXAMPLE 7  | 470  | 14.2 | 21.5 | 27.7 | 31  | 300  |
| EXAMPLE 8  | 510  | 20.0 | 18.1 | 26.7 | 36  | 150  |
| EXAMPLE 9  | 650  | 12.5 | 25.7 | 27.0 | 92  | 500  |
| EXAMPLE 10 | 1056 | 6.6  | 18.2 | 22.9 | 55  | 1000 |
| EXAMPLE 11 | 490  | 7.4  | 30.5 | 25.1 | 60  | 840  |

A: Weighing (g/m²)
B: Water Content (% by Weight)
C: Absorbency (g/g)
D: Absorbency under Load (g/g)
E: Absorbing Rate (seconds)
F: Flexibility (mgf)

As can be seen from the results shown in Table 2, by reducing the water content from the water-containing gel under an applied load, even when adopting the water-containing gel composition, compared with the case of applying only either one of heat and pressure, or the case of applying heat and pressure separately, the absorbent material which shows still improved absorbing properties including absorbency under load and the absorbing rate can be obtained. Furthermore, according to the present embodiment, a sheet-like absorbent material which is excellent in its absorbency under load, absorbing rate and flexibility can be obtained.

Additionally, the compression ratio was measured with respect to the respective sheet-like absorbent materials of Examples 1 through 11. The compression ratio of the absorbent materials of Examples 1 through 11 falls in a range of from 10 to 100, and the absorbent materials show excellent properties in their absorbing rates, etc., compared with the absorbent materials of comparative examples 1 through 3. Not only for the primary order particles of the water-containing gel, but also for the sheet-like absorbent materials, the compression ratio can be determined in the same manner as the aforementioned method. Additionally, the absorbent resin in each absorbent material recovers in the original state before being compressed by swelling (calendaring), thereby showing an excellent absorbency retaining property.

EXAMPLE 12

The reaction and operations of Example 1 were repeated to obtain a water-containing gel. Then, without mixing glycerol (polyvalent alcohol), the surface cross-linking agent (B), and the polyester fibers (subsidiary molding compounds) with the water-containing gel, the water-containing gel was calendared and heated in the same manner as Example 1. Namely, the calendaring and heating processes were carried out with respect to only the water-containing gel as the water-containing gel composition.

Thereafter, 200 g of the resulting absorbent material were placed in the mixer, and were pulverized into a powdery form for 15 seconds. Next, the powdery absorbent material was classified by the JIS standard sieve having an opening of 500 μm to remove coarse granules, thereby obtaining a powdery absorbent material in accordance with the present invention.

The absorbent material resulting from calendaring and heating the water-containing gel was very fragile, and a sheet-like absorbent material could not be obtained directly from the water-containing gel. Namely, when calendaring and heating the water-containing gel in a presence of a polyhydric alcohol, a sheet-like absorbent material could not be obtained. However, the powdery absorbent material resulting from drying and subsequently classifying the absorbent material showed excellent absorbing properties such as absorbency of 42.5 g/g, the absorbency under load of 11.3 g/g, and absorbing rate of 25 seconds. The results of measurement of the absorbent material are described in Table 3.

COMPARATIVE EXAMPLE 4

The water-containing gel of Example 12 was dried in hot air for 1 hour, and was classified by the JIS standard sieve having an opening of 500 μm after pulverizing 200 g of the resulting dried material by a desk top pulverizer, thereby obtaining a powdery absorbent material by removing coarse granules. Then, the results of measurement of the absorbent material are shown in Table 3.

COMPARATIVE EXAMPLE 5

A mixture of the resulting powdery absorbent material from Comparative Example 4 and the polyhydric alcohol was pressurized under an applied heat according to the method of U.S. Pat. No. 4,066,583.

Namely, first, in a predetermined container, 8 g of the powdery absorbent material resulting from Comparative Example 5 and 2 g of glycerol (polyvalent alcohol) were placed, and they were quickly mixed uniformly, thereby obtaining a powdery mixture. After uniformly placing the mixture in a size of 10 cm square, the mixture was placed in the isothermic room having constant humidity adjusted to have a temperature of 25° C. and a relative humidity of 90 percent, and was left for 10 minutes to improve properties of the mixture. After the humidity was applied to the mixture, the powdery absorbent material was formed into a sheet in which powdery absorbent materials are agglomerated, and had a shape retaining propriety which allows it to be lifted up slowly.

Next, using a heat application type compressor, pressure was applied to the sheet-like mixture for 5 minutes at a temperature of 150° C. and under load of 350 gf/cm$^2$. As a result, a transparent sheet-like molding having a thickness of 1 mm was obtained. Next, by adding water to the resulting sheet-like molding so as to have a water content of 17.0 percent by weight, the sheet-like absorbent material was obtained. The results of measurements of the absorbent material were summarized in Table 3.

EXAMPLE 13

The reaction and operations of Example 1 were repeated to obtain a water-containing gel. Next, after mixing only 0.31 g of the surface cross-linking agent (B) to the water-containing gel, calendaring and heating processes were applied in the same manner as Example 1. Namely, using a mixture of the water-containing gel and the surface cross-linking agent (B) as a water-containing gel composition, calendaring and heating processes were carried out. Thereafter, 200 g of the resulting absorbent material was pulverized and classified in the same manner as Example 12, thereby obtaining powdery absorbent material.

The absorbent material obtained in this Example by calendaring and heating the water-containing composition was also very fragile, and a sheet-like absorbent material could not be obtained. Namely, as the water-containing gel was subjected to the calendaring and heating processes in an absence of polyhydric alcohol, the sheet-like absorbent material could not be obtained. However, by carrying out the processes of calendaring and heating the water-containing gel composition simultaneously, an absorbent material which shows excellent absorbing properties such as the absorbing rate, the absorbency under load, especially the absorbing rate could be obtained. The results of measurements of the absorbent material are also shown in Table 3.

COMPARATIVE EXAMPLE 6

Except that instead of calendaring and heating the water-containing gel composition, the water-containing gel was dried for 1 hour in a hot air at 160° C., and after pulverizing 200 g of the resulting dried material by the desk top pulverizer, they were classified by the JIS standard sieve with an opening of 500 μm to remove coarse granules, the reaction and operations of Example 13 were repeated, thereby obtaining a powdery absorbent material. The results of measurements of the absorbent material are also described in Table 3.

COMPARATIVE EXAMPLE 7

2 g of glycerol was mixed with 8 g of powdery absorbent material resulting from Comparative Example 6, and in the same manner as Comparative Example 5, a sheet-like absorbent material having a thickness of 1 mm was obtained. Then, to the sheet-like molding article, water was added so as to have a water content of 19.2 percent by weight, thereby obtaining a sheet-like absorbent material.

The results of measurements of the absorbent material are summarized in Table 3.

EXAMPLE 14

In a 20 liters reaction container equipped with an agitator, a reflux condenser, a thermometer, a nitrogen gas inlet tube and a dropping funnel, 10 litters of cyclohexane and 40 grams of sucrose fatty acid ester (trade name: DK-ESTER F-50, available from Dai-Ichi Kogyo Seiyaku Ltd.) as a surface active agent having 6 HLBs (hydrophile-lipophile balance) were placed, and the content in the reaction container was stirred. After the sucrose fatty acid ester was dissolved in the cyclohexane, nitrogen gas was introduced in the reaction container to replace the air with nitrogen gas.

On the other hand, in 3,030 g of 35 percent by weight aqueous solution of acrylic acid (monomer component) and sodium acrylate (monomer component) (75 mole percent of the total monomer components in the aqueous solution is neutralized), 0.16 g of N,N'-methylene bisacrylamides as a cross-linking agent and 5.3 g of hydroxyethylcellulose (as a thickening agent (trade name: EP-850, available from Daicel Chemical Industries Ltd.) were dissolved to obtain a monomer solution. Then, after removing the oxygen remaining in the solvent by introducing nitrogen gas into the monomer aqueous solution, 1.6 g of potassium persulfate were added as a polymerization initiator to be dissolved therein.

Thereafter, the monomer solution having the polymerization initiator dissolved therein was added to the aqueous solution in the reaction container as a reaction solution. Then, the reaction solution was subjected to a reverse phase suspension polymerization while stirring the reaction solution for two hours at 60° C., thereby obtaining a sphere gel-like polymer. Then, the resulting gel-like polymer was dehydrated by forming an azeotrope and the gel-like polymer was reacted in the reaction container, thereby obtaining dehydrated polymer having an average particle diameter of 480 μm. Thereafter, the resulting dehydrated polymer was classified by a JIS standard sieve to have the dehydrated polymer having a uniform particle diameter in a range of from 500 to 600 μm.

Thereafter, to 100 parts by weight of the dehydrated polymer, 0.05 parts of ethylene glycol diglycidyl ether (surface cross-linking agent (B)) as a cross-linking agent, and an aqueous solution of a crosslinking agent composed of 3 parts by weight of water and 2 parts by weight of isopropanol were added, thereby obtaining a secondary cross-linked polymer by carrying out a surface cross-linkage at 200° C. The water content of the gel-like polymer was reduced without applying a pressure. As a result, the secondary cross-linked polymer is a complete sphere shape having an average particle diameter of 480 μm.

Thereafter, the secondary cross-linked polymer was expanded by adding water, thereby obtaining a water-containing gel of the secondary cross-linked polymer having a 35 percent by weight solid portion. The reaction and operations of Example 1 were repeated with respect to the water-containing gel of the secondary cross-linked polymer with applications of heat and pressure, thereby obtaining the absorbent material in a powdery form.

After undergoing calendaring and heating processes, 100 disk-shaped secondary cross-linked polymer particles having an average thickness of 0.07 mm and an average diameter of 2.60 mm were obtained. Therefore, the compression ratio X in the compressing direction (thickness direction) of the secondary cross-linked polymer particles after undergoing calendaring and heating processes was 0.07/0.48, the expansion ratio Y in the milling direction was 2.60/0.48, and the compression ratio Y/X defined in the present invention was 37. Namely, the secondary cross-linked polymer particles in the absorbent material were compressed by 37 times compared with the state before undergoing calendaring and heating processes. Therefore, the absorbent material composed of the secondary cross-linked polymer particles had high absorbing rate (48 seconds) by a distortion energy in the secondary cross-linked polymer particles, and the absorbent resin was expanded when absorbing water, and was restored into a shape (spherical shape). The results of the measurements of the absorbent material are summarized in table 3.

COMPARATIVE EXAMPLE 8

Reaction and operations of Example 14 were repeated, and a secondary cross-linked polymer was obtained. The respective performances of the resulting secondary cross-linked polymer were measured directly as a comparative absorbent material. Namely, the absorbent material was not compressed, and the compression ratio was 1. The results of measurement of the absorbent material are summarized in Table 3.

TABLE 3

|  | A | B | D | E | F | G |
|---|---|---|---|---|---|---|
| Example 12 | powders | 6.55 | 42.5 | 11.3 | 25 | — |
| Comp. Example 4 | powders | 6.44 | 42.0 | 10.0 | 35 | — |
| Comp. Example 5 | 928 | 17.00 | 31.5 | 4.5 | 680 | 410 |
| Example 13 | powders | 5.11 | 34.6 | 28.4 | 21 | — |
| Comp. Example 6 | powders | 5.22 | 34.0 | 27.8 | 32 | — |
| Comp. Example 7 | 963 | 19.22 | 22.4 | 9.8 | 580 | 380 |
| Example 14 | powders | 5.11 | 45.3 | 27.4 | 25 | — |
| Comp. Example 8 | powders | 0.5> | 44.4 | 27.0 | 48 | — |

A: Weighing (g/m$^2$)
B: Water Content (% by Weight)
C: Absorbency (g/g)
D: Absorbency under Load (g/g)
E: Absorbing Rate (seconds)
F: Flexibility (mgf)

The results shown in Table 3 show that by reducing the water content of the water-containing gel under load, even when adopting the same water-containing gel composition, compared with the case where the gel is heated without applying pressure, powdery absorbent material of still improved absorbency under load and absorbing rate can be obtained. Additionally, according to the conventional method, by forming it into a sheet by once powdering them, the absorbing rate and absorbency under load are significantly reduced, and a sheet-like absorbent material which shows excellent absorbing properties such as absorbency under load and absorbing rate cannot be achieved.

Additionally, from the comparison between Example 14 and comparative example 8, it can be seen that as the resulting absorbent material contains compressed absorbent resin, by the distortion of the cross-linked structure of the absorbent resin, a still improved absorbing rate can be obtained.

EXAMPLE 15

In a reaction container equipped with a thermometer, a nitrogen gas inlet tube, an agitator, 1,000 g of 30 weight percent aqueous solution of acrylic acid (monomer component) and sodium acrylate (monomer component) (75 mole percent of the total monomer components is neutralized) were added, and 1.63 g of the cross-linking agent (C) were placed to form a reaction solution, and nitrogen gas was introduced therein to replace the reaction system with nitrogen gas.

While maintaining the reaction solution at 25° C., 2,2'-azobis(2-amidinopropane) diacrylate (hereinafter referred to as a foaming agent (E)) as the foaming agent was added thereto, and was uniformly dispersed. Thereafter, in an atmosphere of nitrogen, sodium persulfate and L-ascorbic acid were added to carry out a polymerization. After an elapsed of time of around 10 minutes, foaming had started. The amount of use of the foaming agent (E) with respect to 100 parts by weight of a solid portion of a monomer component is 0.2 percent by weight, and an amount of use of sodium persulfate with respect to the monomer component is 0.14 mole percent, and an amount of use of L-ascorbic acid is 0.0008 mole percent.

After carrying out a polymerization for 60 minutes, the resulting bulk-like cellular gel (porous water-containing gel) that was expanded by around 1.05 times was cut into pieces so as to have a particle diameter of from 0.5 mm to 2 mm, thereby obtaining cellular gel having a water content of 70 percent by weight. The solid portion of the cellular gel was 30 percent by weight, and had an average porosity diameter of 150 μm. Additionally, the BET specific area resulting from drying the cellular gel was 0.05 m$^2$/g.

Then, 1,000 g of the cellular gel cut into fine pieces were placed into a stainless lidded two-arm type kneader with two sigma blades and a jacket like that adopted in Example 1. On the other hand, a mixed solution of 95 g of glycerol as polyhydric alcohol and 1.9 g of the surface cross-linking agent (B) was prepared. Then, the cellular gel was heated by passing a hot water of 70° C. through the jacket with stirring. Thereafter, by adding the mixed solution to the cellular gel with stirring, they were kept stirring to be uniformly mixed.

To the resulting mixture, 12.5 g of polyester fiber (subsidiary forming material) made of polyethylene terephthalate having a length in a range of from 20 mm to 30 mm were gradually added, and were kneaded until clod no longer existed, thereby obtaining a cellular gel composition including a cellular gel having a dried average particle diameter of 400 μm.

Thereafter, the cellular gel composition was calendared using the same single drum dryer of Example 1, and the miller, and the surface in contact with the drum dryer of the cellular gel composition was heated to 150° C. by the dryer drum. Then, the resulting sheet was scraped off by the scraper, thereby obtaining a flexible sheet-like absorbent material that can be bent 180°.

The resulting absorbent material had a weight of 170 g/m$^2$, water content of 9.0 percent by weight, absorbency of 20 g/g, absorbency under load of 31 g/g and a absorbing rate of 13 seconds. The results of measurements and essential conditions for manufacturing the cellular gel composition are summarized in Table 4. By absorbing water, the cellular gel was swollen to the original state before being milled, and the absorbent material was curled in an opposite direction to the curved surface of the dryer drum.

EXAMPLE 16

The reaction and operations of Example 15 were repeated except that the foaming agent (E) was not used when carrying out a polymerization reaction, and non-cellular gel was obtained. Then, in the same manner as Example 15, a sheet-like absorbent material was obtained. The results of measurements of the absorbent material and the essential conditions of manufacturing the water-containing gel composition of the present invention are summarized in Table 4.

EXAMPLE 17

An expansion polymerization was carried out in the same manner as Example 15 except that in place of the foaming agent (E), sodium carbonate (hereinafter referred to as a foaming agent (F)) was used in an amount of 2.5 percent by weight with respect to 100 parts by weight of a solid portion of the monomer component, and a surface active agent of polyoxyethylene sorbitan monostearate (hereinafter referred to as dispersion stabilizer (G)) was used as a dispersion stabilizer of the foaming agent in an amount of 0.1 percent by weight with respect to 100 parts by weight. Then, the resulting bulk-like cellular gel that was expanded to about two times (porous water-containing gel) was cut into fine pieces, thereby obtaining a cellular gel having a water content of around 70 percent by weight that was cut into pieces having a particle diameter in a range of from 0.5 mm and 2 mm. The solid portion of the cellular gel was 30 percent by weight, and had an average porosity diameter of 200 μm. The BET surface area of the dried cellular gel was 0.05 m²/g.

Thereafter, 1,000 g of finely divided cellular gel were placed in a kneader having the same arrangement as the kneader adopted in Example 15. A mixed solution of 75 g of glycerol as a polyhydric alcohol and 1.5 g of the surface cross-linking agent (B) were prepared. Next, the cellular gel was heated with stirring by passing hot water of 70° C. through the jacket. Thereafter, the resulting mixed solution was added to the cellular gel until they were uniformly mixed.

To the resulting mixture, 13.5 g of polyester fibers (subsidiary forming material) made of polyethylene terephthalate having a length in a range of from 20 mm to 30 mm were gradually added, and were kneaded until clod of the fibers no longer existed, thereby obtaining a cellular gel composition including a cellular gel having a dried average particle diameter of 350 μm.

Thereafter, the cellular gel composition was calendared and was scraped off by the scraper in the same manner as Example 15, thereby obtaining a flexible sheet-like absorbent material that can be bent 180°.

The resulting absorbent material had a weight of 300 g/m², water content of 10.0 percent by weight, absorbency of 23 g/g, absorbency under load of 27 g/g and a absorbing rate of 19 seconds. The results of measurements and essential conditions for manufacturing the cellular gel composition were summarized in Table 4. By absorbing water, the cellular gel was swollen to the original state before being milled, and the absorbent material was curled in an opposite direction to the curved surface of the drum dryer so as to have a low temperature surface inside.

EXAMPLE 18

The reaction and operations of Example 17 were repeated except that the foaming agent (F) was not used when carrying out a polymerization reaction, and non-cellular gel was obtained. Then, in the same manner as Example 17, a sheet-like absorbent material was obtained. The results of measurements of the absorbent material and the essential conditions of manufacturing the water-containing gel composition of the present invention are summarized in Table 4.

TABLE 4

| | EXAMPLE | | | |
|---|---|---|---|---|
| | 15 | 16 | 17 | 18 |
| SOLID PORTION (% BY WEIGHT) | 30 | 30 | 30 | 30 |
| CROSS-LINKING AGENT (C) (g) | 1.63 | 1.63 | 1.63 | 1.63 |
| SURFACE CROSS-LINKING AGENT (B) (g) | 1.9 | 1.9 | 1.5 | 1.5 |
| FOAMING AGENT (E) (% BY WEIGHT) | 0.2 | — | — | — |
| FOAMING AGENT (F) (% BY WEIGHT) | — | — | 2.5 | — |
| DISPERSION STABILIZER (G) (% BY WEIGHT) | — | — | 0.1 | 0.1 |
| GLYCEROL (g) | 95 | 95 | 75 | 75 |
| POLYESTER FIBERS (g) | 12.5 | 12.5 | 13.5 | 13.5 |
| (mm) | 20–30 | 20–30 | 20–30 | 20–30 |
| WEIGHT (g/m) | 170 | 175 | 300 | 310 |
| WATER CONTENT (% BY WEIGHT) | 9.0 | 9.5 | 10.0 | 11.1 |
| ABSORBENCY (g/g) | 20 | 20 | 23 | 23 |
| ABSORBENCY UNDER LOAD (g/g) | 31 | 30 | 27 | 26 |
| ABSORBING RATE (seconds) | 13 | 40 | 19 | 45 |
| FLEXIBILITY (mgf) | 480 | 490 | 560 | 570 |

As is clear from the results shown in Table 4, the absorbent material resulting from the manufacturing method of the present invention had excellent properties especially in absorbency under load and absorbing rate. The results also proved that the absorbent materials produced from the cellular gel as a gel were superior to those produced from the non-cellular gel in their absorbing rate, absorbency under load, etc.

EXAMPLE 19

The reaction and the operations of Example 4 were repeated, and a sheet-like absorbent material was obtained. Then, the resulting absorbent material was cut into a piece of 12 cm×25 cm size. On the other hand, non-woven fabrics were taken out from paper diapers (Pampers L-size (product name) available from Proctor & Gamble (P&G) Co.), and the non-woven fabrics were cut into the same size as the absorbent material. Then, the non-woven fabrics were laminated on the absorbent material, thereby obtaining a simple absorbing member as an example of the absorbent article.

The performances of the resulting simple absorbing member were determined. Specifically, the simple absorbing member was placed on an acryl plate, and another acryl plate was placed on the simple absorbent member. The upper acryl plate had a liquid introducing tube having an inner diameter of 23 mm at a position corresponding to a central portion of the simple absorbent member. Then, with respect to the simple absorbent member, a load of 23 g/cm² was uniformly applied to the simple absorbent member.

In this state, 50 ml of physiologic saline solution was poured into a liquid tube, and the time required from the state till the completion of absorbing the physiologic saline by the absorbent in a simple manner was measured, to set the time as the absorbing time (seconds). Then, the operation was repeated three times every 5 minutes, and after an elapse of 5 minutes from the completion of the third operation, the upper acryl plate and the weight were taken out, and 10 pieces of kitchen towels (Nepia, available from Shin Oji Paper Co., Ltd.) were placed on the sample absorbing member. Thereafter, the upper acryl plate and the weight were placed thereon again. The weight of the kitchen towel was measured beforehand.

After an elapse of 1 minutes from the completion of the described operation, the weight of the kitchen towel was measured. The weight obtained by extracting the original weight from the weight after the operation was determined to be a return weight (g).

The absorbing times of the first, second and third operations were 535 seconds, 1185 seconds and 610 seconds respectively, and the return weight was 11.97 g.

Possible Industial Use of the Invention

The absorbent resin and the absorbent material of the present invention have excellent absorbing properties such as absorbing rate, absorbency under load and shape retaining property. For these beneficial features, the absorbent resin and the absorbent material of the present invention are suited for use in absorbent articles, for example, sanitary materials such as paper diapers (disposable diapers), sanitary napkins, so-called incontinence pads, etc., moisture condensation absorbent sheets, which are desired to have higher performances and to be made thinner. Therefore, the present invention offers the described absorbent articles of excellent performances.

We claim:

1. An absorbent resin which is characterized by anisotropically swelling against distortion from a compressed and distorted state into a non-similar shape by absorbing an aqueous solution and which is made of a water-containing gel capable of absorbing an aqueous fluid in an amount of not less than three times the weight of the gel.

2. The absorbent resin as set forth in claim 1, characterized by being compressed at a ratio of compression in a range of from 2 to 1,000.

3. The absorbent resin as set forth in claim 2, characterized by having a distorted cross-linked structure by compression.

4. An absorbent resin as defined in claim 2, characterized by restoring its original shape before being compressed.

5. The absorbent resin as set forth in claim 1, characterized by having foams inside.

6. An absorbent material comprising:
    an absorbent resin which anisotropically swells against distortion from a compressed and distorted state into a non-similar shape by absorbing an aqueous solution and which is made of a water-containing gel capable of absorbing an aqueous fluid in an amount of not less than three times the weight of the gel, and being formed into a sheet so as to have a flexibility of not more than 1,000 mgf.

7. The absorbent material as set forth in claim 6, characterized by being swollen by absorbing water so as to have a curvature.

8. A method of manufacturing an absorbent material, comprising
    reducing an amount of an aqueous solvent in a water-containing gel of a hydrophilic cross-linked polymer while compressing said water-containing gel to produce an absorbent resin which anisotropically swells against distortion from a compressed and distorted state into a non-similar shape by absorbing an aqueous solution, said water-containing gel being capable of absorbing an aqueous fluid in an amount of not less than three times the weight of the gel and,
    molding said adsorbent resin into a sheet.

9. The method of manufacturing an absorbent material as set forth in claim 8, characterized in that:
    said water-containing gel further includes polyhydric alcohol.

10. The method of manufacturing an absorbent material as set forth in claim 8, characterized in that a water content of said water-containing gel is in a range of from 30 percent by weight to 90 percent by weight.

11. The method of manufacturing as set forth in claim 8, characterized by including the step of calendaring said water-containing gel to be formed into a sheet.

12. The method of manufacturing an absorbent material a set forth in claim 11, characterized by carrying heating and pressurizing processes simultaneously so as to generate a temperature difference between a first surface and a second surface of the sheet.

13. A method of manufacturing an absorbent material, comprising
    compressing a cellular gel of a hydrophilic cross-linked polymer to produce an absorbent resin which anisotropically swells against distortion from a compressed and distorted state into a non-similar shape by absorbing an aqueous solution, said cellular gel being a water-containing gel capable of absorbing an aqueous fluid in an amount of not less than three times the weight of the gel and,
    molding said absorbent resin into a sheet.

14. The method of manufacturing the absorbent material as set forth in claim 13, characterized in that:
    said cellular gel further comprises polyhydric alcohol.

15. The method of manufacturing the absorbent material as set forth in claim 13, characterized in that:
    a water content of said cellular gel is in a range of from 30 percent by weight to 90 percent by weight.

16. The method of manufacturing an absorbent material as set forth in claim 13, characterized in that:
    an amount of aqueous solvent in said cellular gel is reduced under an applied pressure.

17. The method of manufacturing an absorbent material as set forth in claim 13, characterized by comprising the step of calendaring said cellular gel to be formed into a sheet.

18. The method of manufacturing an absorbent material as set forth in claim 17, characterized by comprising the step of carrying out pressurizing and heating processes simultaneously so as to generate a temperature difference between a first surface and a second surface of the sheet.

19. The absorbent resin as set forth in claim 1, characterized by being prepared by compressing a water-containing gel of a hydrophilic cross-linked polymer.

20. The absorbent resin as set forth in claim 19, characterized in that:
    the water-containing gel is a gel-like hydrophilic cross-linked polymer prepared by polymerizing a monomer component including an ethylenically unsaturated monomer using an aqueous solvent.

21. The absorbent resin as defined in claim 20, characterized in that:
    said hydrophilic cross-linked polymer has a three-dimensional net structure, an inside portion thereof being cross-linked by a cross-linking agent, and said cross-linking agent is used in an amount ranging from 0.001 mole percent to 2 mole percent based on the amount of the monomer component.

22. The absorbent resin as set forth in claim 19, characterized in that:
    said hydrophilic cross-linked polymer is a cross-linked poly(meth)acrylic acid (salt).

23. The absorbent resin as defined in claim 19, characterized in that the water-containing gel includes a water-soluble component in a range of from 0.1 percent by weight to 20 percent by weight.

24. The absorbent resin as defined in claim 2, characterized in that:

said compression ratio is Y/X, wherein X is a compression ratio in a direction of compressing the absorbent resin, and Y is an expansion ratio in an expanding direction of the absorbent resin.

25. An absorbent material as defined in claim 6, characterized in that said absorbent resin is prepared by compressing a water-containing gel of a hydrophilic cross-linked polymer.

26. The absorbent material as set forth in claim 25, characterized in that:

the water-containing gel is a gel-like hydrophilic cross-linked polymer prepared by polymerizing a monomer component including an ethylenically unsaturated monomer using an aqueous solvent.

27. The absorbent material as defined in claim 26, characterized in that:

said hydrophilic cross-linked polymer has a three-dimensional net structure, an inside portion thereof being cross-linked by a cross-linking agent, and said cross-linking agent is used in an amount ranging from 0.001 mole percent to 2 mole percent based on the amount of the monomer component.

28. The absorbent material as set forth in claim 25, characterized in that said hydrophilic cross-linked polymer is a cross-linked poly(meth)acrylic acid (salt).

29. The absorbent material as defined in claim 25, characterized in that:

said water-containing gel has cells inside.

30. The absorbent material as defined in claim 25, characterized in that:

said water-containing gel includes a water-soluble component in a range of from 0.1 percent by weight to 20 percent by weight.

31. The absorbent material as defined in claim 25, characterized in that:

a compression ratio of said water-absorbent resin is in a range of from 2 to 1,000.

32. The absorbent material as defined in claim 31 characterized in that:

said compression ratio is Y/X, wherein X is a compression ratio in a direction of compressing the absorbent resin, and Y is an expansion ratio in an expanding direction of the absorbent resin.

33. The absorbent material as set forth in claim 6, characterized in that:

an absorbing rate of the material is not less than 150 seconds.

34. The absorbent material as set forth in claim 6, characterized in that:

said material has an absorbency under pressure is not less than 15 g/g.

35. The method of manufacturing an absorbent material as set forth in claim 8, characterized in that:

from 10 to 90 percent by weight of an aqueous solvent of the water-containing gel of the hydrophilic cross-linked polymer is reduced before being compressed.

36. The method of manufacturing an absorbent resin as defined in claim 8, characterized in that:

a conversion of said water-containing gel is in a range of from 90 to 99.99%.

37. The method of manufacturing an absorbent material as set forth in claim 8, characterized in that the water-containing gel is a gel-like hydrophilic cross-linked polymer prepared by polymerizing a monomer component including an ethylenically unsaturated monomer using an aqueous solvent.

38. The method of manufacturing an absorbent material as set forth in claim 37, characterized in that:

said hydrophilic cross-linked polymer has a three-dimensional net structure, an inside portion thereof being cross-linked by a cross-linking agent, and said cross-linking agent is used in an amount ranging from 0.001 mole percent to 2 mole percent based on the amount of the monomer component.

39. The method of manufacturing an absorbent material as set forth in claim 8 characterized in that:

said hydrophilic cross-linked polymer is a cross-linked poly(meth)acrylic acid (salt).

40. The method of manufacturing an absorbent material as set forth in claim 8, characterized in that:

the water-containing gel includes a water-soluble component in a range of from 0.1 percent by weight to 20 percent by weight.

41. The method of manufacturing an absorbent material as set forth in claim 13, characterized in that:

a conversion of said cellular gel is in a range of from 90 percent to 99.99 percent.

42. The method of manufacturing an absorbent material as set forth in claim 13, characterized in that said cellular gel is a gel-like hydrophilic cross-linked polymer prepared by polymerizing a monomer component including an ethylenically unsaturated monomer using an aqueous solvent in a presence of a foaming agent.

43. The method of manufacturing an absorbent material as set forth in claim 42, characterized in that:

said hydrophilic cross-linked polymer has a three-dimensional net structure, an inside portion thereof being cross-linked by a cross-linking agent, and said cross-linking agent is used in an amount ranging from 0.001 mole percent to 2 mole percent based on the amount of the monomer component.

44. The method of manufacturing an absorbent material as set forth in claim 13, characterized in that:

said hydrophilic cross-linked polymer is a cross-linked poly(meth)acrylic acid (salt).

45. The method of manufacturing an absorbent material as set forth in claim 13, characterized in that:

the water-containing gel includes a water-soluble component in a range of from 0.1 percent by weight to 20 percent by weight.

46. The method of manufacturing an absorbent material as set forth in claim 16, characterized in that:

from 10 to 90 percent by weight of an aqueous solvent of a water-containing gel of the hydrophilic cross-linked polymer before being compressed is reduced.

* * * * *